(12) United States Patent
Hamrah et al.

(10) Patent No.: US 11,998,270 B2
(45) Date of Patent: Jun. 4, 2024

(54) SYSTEM FOR DETECTING MICRO-NEUROMAS AND METHODS OF USE THEREOF

(71) Applicants: Tufts Medical Center, Inc., Boston, MA (US); President and Fellows of Harvard College, Cambridge, MA (US)

(72) Inventors: Pedram Hamrah, Wellesley, MA (US); Neslihan Dilruba Koseoglu, Boston, MA (US); Andrew Beam, Boston, MA (US)

(73) Assignees: Tufts Medical Center, Inc., Boston, MA (US); President and Fellows of Harvard College, Cambridge, MA (US)

( * ) Notice: Subject to any disclaimer, the term of this patent is extended or adjusted under 35 U.S.C. 154(b) by 764 days.

(21) Appl. No.: 17/051,905

(22) PCT Filed: Apr. 26, 2019

(86) PCT No.: PCT/US2019/029496
§ 371 (c)(1),
(2) Date: Oct. 30, 2020

(87) PCT Pub. No.: WO2019/212911
PCT Pub. Date: Nov. 7, 2019

(65) Prior Publication Data
US 2021/0113078 A1     Apr. 22, 2021

Related U.S. Application Data

(60) Provisional application No. 62/664,734, filed on Apr. 30, 2018.

(51) Int. Cl.
*A61B 3/00*     (2006.01)
*A61B 3/10*     (2006.01)
(Continued)

(52) U.S. Cl.
CPC .......... *A61B 3/0025* (2013.01); *A61B 3/1025* (2013.01); *A61B 3/13* (2013.01);
(Continued)

(58) Field of Classification Search
CPC ....... A61B 3/0025; A61B 3/1025; A61B 3/13; A61B 3/14; G06T 7/0012
(Continued)

(56) References Cited

U.S. PATENT DOCUMENTS

2002/0186875 A1    12/2002  Burmer et al.
2008/0088918 A1    4/2008   O'Connell
(Continued)

FOREIGN PATENT DOCUMENTS

JP    2013-540995 A  * 11/2013

OTHER PUBLICATIONS

Dieckmann et al., "Neuropathic Corneal Pain: Approaches for Management," Ophthalmology 124(11S):S34-S47(2017) (Year: 2017).*
(Continued)

*Primary Examiner* — James R Greece
(74) *Attorney, Agent, or Firm* — Clark & Elbing LLP; Susan M. Michaud

(57) ABSTRACT

The invention provides methods of diagnosing neuropathic corneal pain by the detection of neuromas, such as micro-neuromas, on the cornea. The invention also features systems for detecting the presence of anatomical features located on an ocular tissue surface that may be a marker for neuropathic corneal pain. The systems feature an in vivo confocal microscope and a computer N programmed with a neural network to automate the analysis of the microscope images. The invention provides methods of using the system to identify a micro-neuroma in images collected of an ocular surface and methods of diagnosing neuropathic corneal pain and monitoring treatment of neuropathic corneal pain using
(Continued)

a system of the invention. The invention further provides a non-transitory computer readable medium having instructions stored thereon, wherein the instructions, when executed by a processor, perform a method for automatically determining the presence of at least one neuroma on a plurality of images of an ocular surface of a patient.

12 Claims, 12 Drawing Sheets

(51) Int. Cl.
  *A61B 3/13* (2006.01)
  *A61B 3/14* (2006.01)
  *G06T 7/00* (2017.01)
(52) U.S. Cl.
  CPC .............. *A61B 3/14* (2013.01); *G06T 7/0012* (2013.01); *G06T 2207/20084* (2013.01); *G06T 2207/30041* (2013.01)
(58) Field of Classification Search
  USPC ........................................ 351/205, 206, 246
  See application file for complete search history.

(56) References Cited

U.S. PATENT DOCUMENTS

2010/0238404 A1* 9/2010 Newman .............. A61B 5/0066
  351/208
2011/0274322 A1 11/2011 Kern et al.

OTHER PUBLICATIONS

Dieckmann et al., "Neuropathic Corneal Pain: Approaches for Management," Ophthalmology 124(11S):S34-S47 (2017).
International Preliminary Report on Patentability for International Application dated Nov. 12, 2020 for PCT International Application No. PCT/US19/29496, Hamrah et al., "System for Detecting Micro-Neuromas and Methods of Use Thereof," filed Apr. 26, 2019 (13 pages).
International Search Report and Written Opinion dated Aug. 22, 2019, for PCT International Application No. PCT/US19/29496, Hamrah et al., "System for Detecting Micro-Neuromas and Methods of Use Thereof," filed Apr. 26, 2019 (20 pages).

* cited by examiner

A

B

A

B

A

B

SYSTEM FOR DETECTING MICRO-NEUROMAS AND METHODS OF USE THEREOF

BACKGROUND

Neuropathic corneal pain (NCP) is one of the most underdiagnosed ocular surface diseases due to a lack of clinical signs explaining patient symptoms. Thus, there is a need in the art to provide a robust system for visualizing and interpreting images of the ocular surface to enable clinicians to accurately diagnose and treat NCP.

SUMMARY

The invention provides methods and systems for diagnosing neuropathic corneal pain and the basis thereof. In some embodiments, the methods of the invention involve detection of neuromas (e.g., micro-neuromas) on patient corneas, wherein detection of the neuromas (e.g., micro-neuromas) is an indication that the patient has neuropathic corneal pain (NCP), rather than (or in addition to) a different condition (e.g., dry eye disease; also see below). Optionally, this detection method is used in combination with one or more other methods, as described herein (e.g., assessment of symptoms of eye discomfort). The methods of the invention can, in some embodiments, be carried out using systems including AI features, such as neural networks (e.g., as described herein).

The invention provides systems for determining of the presence of at least one neuroma (e.g., a micro-neuroma) on an ocular surface (e.g., a corneal surface) of a subject (e.g., a human subject), the systems including: (a) an in vivo confocal microscope configured to produce an image of at least a portion of the ocular surface; and (b) a computer programmed to determine the presence of at least one neuroma on the ocular surface from input data corresponding to the image produced by the in vivo confocal microscope. The system can optionally be used as a diagnostic system or as a supportive biomarker for diagnosis. Further, the system can be used to assess therapeutic efficacy. In addition, it can be used in case a patient has other symptoms of neurosensory abnormalities, such as light sensitivity, burning, or dryness. Furthermore, the diagnostic methods described herein can be carried out in conjunction with consideration of symptoms of discomfort.

In various embodiments, the computer is programmed with a neural network, which may optionally be or include a multilayer perceptron. In various embodiments, the multilayer perceptron includes one or more of: (a) a plurality of input nodes, wherein each input node is configured to contain at least one data point; (b) a plurality of hidden nodes grouped in at least one layer, wherein each of the plurality of hidden nodes receives as input all of the at least one data points from the plurality of input nodes; and (c) a plurality of output nodes, where the plurality of hidden nodes and plurality of output nodes are trained with a plurality of images of an ocular surface.

In various embodiments, the plurality of hidden nodes further includes a transfer function (e.g., a sigmoid function) to determine the presence of at least one micro-neuroma in an eye of a subject. In various embodiments, the derivative of the transfer function is used to update the statistical weights of each of the plurality of hidden nodes. In various embodiments, the plurality of output nodes further includes a sigmoid transfer function.

In various embodiments, the neural network is trained using a plurality of images (e.g., at least 1,000 or at least 10,000) images of an ocular surface from, e.g., a population of subjects. In various embodiments, a portion of the plurality of images of the ocular surface from the population of subjects includes images of micro-neuromas.

In various embodiments, the input data for the neural network is a function of the response of the in vivo confocal microscope. Optionally, the input data for the neural network is normalized to values between 0-1.

In various embodiments, the plurality of output nodes return a value representative of the presence of a neuroma (e.g., a micro-neuroma) on an ocular surface (e.g., a corneal surface) of a subject.

In various embodiments, the computer (a) communicates wirelessly with the in vivo confocal microscope; (b) is directly connected to the in vivo confocal microscope; (c) is part of the in vivo confocal microscope; and/or (d) communicates remotely with the in vivo confocal microscope.

The invention also provides methods of identifying the presence of a neuroma (e.g., a micro-neuroma) on an ocular surface (e.g., a corneal surface) of a subject (e.g., a human), including: (a) directing light from an in vivo confocal microscope onto the ocular surface of the subject to produce an image of at least a portion of the ocular surface; (b) sending the image to a computer programmed with a neural network to determine the presence of a neuroma; and (c) storing or providing the result of (b) to a user.

In various embodiments, the neural network is trained using a plurality of images (e.g., at least 1,000 or at least 10,000) images of an ocular surface from, e.g., a population of subjects. In various embodiments, a portion of the plurality of images of the ocular surface from the population of subjects includes images of micro-neuromas.

The invention further provides methods of differentially diagnosing neuropathic corneal pain from another ocular indication in a subject (e.g., a human), including: (a) acquiring an image of at least a portion of an ocular surface (e.g., a corneal surface) of the subject; (b) sending the image to a computer programmed to provide an analysis of the ocular surface; and (c) storing or displaying the image and/or analysis of the ocular surface to the user, where the resulting image and/or analysis of the ocular surface indicates the presence or absence of at least one parameter associated with neuropathic corneal pain.

In various embodiments, the other ocular indication includes dry eye disease, complications from refractive surgery, ocular effects of Sjögren's Syndrome, neuralgia associated with herpes viruses, chemical irritations, side effects of pharmaceuticals, chemotherapy, and radiation therapy.

In various embodiments, the method further includes administration of a therapeutic agent suitable for treating neuropathic corneal pain. In various embodiments, the therapeutic agent is administered ocularly, parenterally, or orally. In various embodiments, the therapeutic agent for ocular or parenteral administration is selected from the group consisting of tricyclic antidepressants, anticonvulsants, autologous serum tears, corticosteroids, cryopreserved amniotic membrane, amniotic fluid, protective contact lenses, scleral lenses, and artificial tears. In various embodiments, the therapeutic agent for oral administration is selected from the group consisting of tricyclic antidepressants, anticonvulsants, opioid antagonists, opioid agonists, GABA inhibitors, serotonin-norepinephrine reuptake inhibitor, transient receptor potential vanilloid (TRPV) receptor antagonists, transient receptor potential melastatin (TRPM) receptor antagonists, and sodium channel blockers.

In various embodiments, the methods include at least one parallel diagnosis test, e.g., at least one parallel diagnosis test selected from the group consisting of an ocular pain questionnaire, functional somatosensory testing, and a physical eye examination.

In various embodiments, the image is acquired using in vivo confocal microscopy. In various embodiments, the computer is programmed with a neural network. In various embodiments, the at least one parameter associated with neuropathic corneal pain is an anatomical structure (e.g., a neuroma, such as a micro-neuroma).

In various embodiments, the neural network is trained using a plurality of images (e.g., at least 1,000 or at least 10,000) images of an ocular surface from, e.g., a population of subjects. In various embodiments, a portion of the plurality of images of the ocular surface from the population of subjects includes images of micro-neuromas.

The invention also provides methods of assessing a treatment regimen for neuropathic corneal pain, including: (a) acquiring a first set of in vivo confocal microscopy images of an ocular surface (e.g., a corneal surface) of a subject (e.g., a human) experiencing neuropathic corneal pain; (b) analyzing the first set of in vivo confocal microscopy images using a computer programmed with a neural network to identify an anatomical structure (e.g., a neuroma, such as a micro-neuroma) associated with neuropathic corneal pain; (c) administering (e.g., ocularly, parenterally, or orally) a therapeutic agent suitable for treating neuropathic corneal pain for a therapeutically sufficient duration (e.g., at least 1, 2, 3, 4, 5, 6, or 7 days, or 2, 3, 4, 5, 6, or 7 weeks); (d) acquiring a second set of in vivo confocal microscopy images of the ocular surface of the subject experiencing neuropathic corneal pain; (e) analyzing the second set of in vivo confocal microscopy images using a computer programmed with a neural network to determine structural changes in the anatomical structure causing neuropathic corneal pain; and (f) repeating steps (a)-(e) until the subject experiences a reduction in neuropathic corneal pain, wherein the reduction of neuropathic pain is caused by a reduction in at least one dimension of the anatomical structure identified by the in vivo confocal microscopy imaging.

In various embodiments, the neural network is trained using a plurality of images (e.g., at least 1,000 or at least 10,000) images of an ocular surface from, e.g., a population of subjects. In various embodiments, a portion of the plurality of images of the ocular surface from the population of subjects includes images of micro-neuromas.

In various embodiments, the therapeutic agent for ocular or parenteral administration is selected from the group consisting of tricyclic antidepressants, anticonvulsants, autologous serum tears, corticosteroids, cryopreserved amniotic membrane, amniotic fluid, protective contact lenses, scleral lenses, and artificial tears.

In various embodiments, the therapeutic agent for oral administration is selected from the group consisting of tricyclic antidepressants, anticonvulsants, opioid antagonists, opioid agonists, GABA inhibitors, serotonin-norepinephrine reuptake inhibitor, transient receptor potential vanilloid (TRPV) receptor antagonists, transient receptor potential melastatin (TRPM) receptor antagonists, and sodium channel blockers.

The invention further provides methods of determining the efficacy of a treatment for neuropathic corneal pain, including: (a) diagnosing a subject (e.g., a human) as having neuropathic corneal pain; (b) acquiring a first set of in vivo confocal microscopy images of an ocular surface (e.g., a corneal surface) of the subject; (c) analyzing the first set of in vivo confocal microscopy images using a computer programmed with a neural network to identify at least one parameter associated with neuropathic corneal pain; (d) administering a therapeutic agent to the subject; (e) acquiring a second set of in vivo confocal microscopy images of the ocular surface of the subject; (f) analyzing the second set of in vivo confocal microscopy images using a computer programmed with a neural network to determine a change in the at least one parameter associated with neuropathic corneal pain; and (g) providing an output indicative of the efficacy of the treatment for neuropathic corneal pain. In various embodiments, the at least one parameter associated with neuropathic corneal pain is an anatomical structure (e.g., a neuroma, such as a micro-neuroma).

In various embodiments, the neural network is trained using a plurality of images (e.g., at least 1,000 or at least 10,000) images of an ocular surface from, e.g., a population of subjects. In various embodiments, a portion of the plurality of images of the ocular surface from the population of subjects includes images of micro-neuromas.

In various embodiments, the therapeutic agent for neuropathic corneal pain is selected from or includes tricyclic antidepressants, anticonvulsants, nerve growth factors, naltrexone, amniotic membrane gel, cryopreserved amniotic membranes, amniotic fluid, dual enkephalinase inhibitors, Tivanisiran (Syl1001), anti-inflammatories, immunosuppressives, lifitegrast, transient receptor potential vanilloid (TRPV) receptor antagonists, transient receptor potential melastatin (TRPM) receptor antagonists, or neuroregeneratives.

In various embodiments, the change in the at least one parameter associated with neuropathic corneal pain is or includes a reduction in at least one dimension of the anatomical structure.

In various embodiments, providing the output is or includes displaying a representation of the data from the neural network to a user on a display device.

The invention further provides non-transitory computer readable media having instructions stored thereon, wherein the instructions, when executed by a processor, perform a method for automatically determining the presence of at least one neuroma on at least one image of an ocular surface of a subject, the method including: a) acquiring at least one image of an ocular surface of a subject; and b) determining the presence of a neuroma (such as a micro-neuroma) on the at least one image of an ocular surface of a subject by analyzing the at least one image of an ocular surface of a subject using a trained neural network, where the trained neural network includes: i) a residual learning architecture; and ii) a backpropagation algorithm comprising a gradient descent optimizer, where the neural network is trained using a plurality of images of an ocular surface from a population of subjects. The plurality of images of an ocular surface from a population of subjects are augmented using data blending augmentation or data interpolating augmentation (e.g., mix-up or manifold mix-up) prior to training by the neural network.

In various embodiments, the at least one image of an ocular surface of a subject are acquired using an in vivo confocal microscope. In various embodiments, the plurality of images of an ocular surface from a population of subjects used to train the neural network are pre-processed by normalizing each image against parameters from an image database. In various embodiments, the plurality of images of an ocular surface from a population of subjects used to train the neural network are pre-processed by conversion of a grayscale single channel pixel intensity to a three channel RGB color pixel intensity. In various embodiments, the plurality of images of an ocular surface from a population of subjects used to train the neural network are further augmented prior to training the neural network by random image flipping, random image rotation, random image crops, or a combination thereof.

In various embodiments, the neural network further includes batch normalization. In various embodiments, the neural network further includes Dropout regularization.

In various embodiments, the residual learning architecture includes an input layer, an output layer, and from 2 to 100 hidden layers, e.g., from 2 hidden layers to 20 hidden layers, from 10 hidden layers to 30 hidden layers, from 20 hidden layers to 40 hidden layers, from 30 hidden layers to 50 hidden layers, from 40 hidden layers to 60 hidden layers, from 50 hidden layers to 70 hidden layers, from 60 hidden layers to 80 hidden layers, from 70 hidden layers to 90 hidden layers, or from 80 hidden layers to 100 hidden layers, e.g., 2 hidden layers, 3 hidden layers, 4 hidden layers, 5 hidden layers, 6 hidden layers, 7 hidden layers, 8 hidden layers, 9 hidden layers, 10 hidden layers, 15 hidden layers, 20 hidden layers, 25 hidden layers, 30 hidden layers, 35 hidden layers, 40 hidden layers, 45 hidden layers, 50 hidden layers, 55 hidden layers, 60 hidden layers, 65 hidden layers, 70 hidden layers, 75 hidden layers, 80 hidden layers, 85 hidden layers, 90 hidden layers, 95 hidden layers, or 100 hidden layers. In various embodiments, the total number of layers of the residual learning architecture is from 3 to 102 layers, e.g., from 3 layers to 20 layers, from 10 layers to 30 layers, from 20 layers to 40 layers, from 30 layers to 50 layers, from 40 layers to 60 layers, from 50 layers to 70 layers, from 60 layers to 80 layers, from 70 layers to 90 layers, or from 80 layers to 102 layers, e.g., 2 layers, 4 layers, 6 layers, 8 layers, 10 layers, 12 layers, 14 layers, 16 layers, 18 layers, 20 layers, 22 layers, 24 layers, 26 layers, 28 layers, 30 layers, 32 layers, 34 layers, 36 layers, 38 layers, 40 layers, 42 layers, 44 layers, 46 layers, 48 layers, 50 layers, 52 layers, 54 layers, 56 layers, 58 layers, 60 layers, 62 layers, 64 layers, 66 layers, 68 layers, 70 layers, 72 layers, 74 layers, 76 layers, 78 layers, 80 layers, 82 layers, 84 layers, 86 layers, 88 layers, 90 layers, 92 layers, 94 layers, 96 layers, 98 layers, 100 layers, or 102 layers. In various embodiments, the total number of layers of the residual learning architecture is from 40-60.

In various embodiments, the gradient descent optimizer includes stochastic gradient descent. In various embodiments, the gradient descent optimizer includes a learning rate from about 0.000001 to about 0.1, e.g., from about 0.000001 to about 0.00001, about 0.000005 to about 0.00005, about 0.00001 to about 0.0001, about 0.00005 to about 0.0005, about 0.0001 to about 0.001, about 0.0005 to about 0.005, about 0.001 to about 0.01, about 0.005 to about 0.05, or about 0.01 to about 0.1, e.g., about 0.000001, about 0.000002, about 0.000003, about 0.000004, about 0.000005, about 0.000006, about 0.000007, about 0.000008, about 0.000009, about 0.00001, about 0.00002, about 0.00003, about 0.00004, about 0.00005, about 0.00006, about 0.00007, about 0.00008, about 0.00009, about 0.0001, about 0.0002, about 0.0003, about 0.0004, about 0.0005, about 0.0006, about 0.0007, about 0.0008, about 0.0009, about 0.001, about 0.002, about 0.003, about 0.004, about 0.005, about 0.006, about 0.007, about 0.008, about 0.009, about 0.01, about 0.02, about 0.03, about 0.04, about 0.05, about 0.06, about 0.07, about 0.08, about 0.09, or about 0.1. In various embodiments, the learning rate is 0.00001.

In various embodiments, the gradient descent optimizer further includes momentum gradient acceleration. In various embodiments, the momentum gradient acceleration has a value from 0 to about 1. In various embodiments, the momentum gradient acceleration has a value of 0.9.

In various embodiments, the neural network is trained using a plurality of images (e.g., at least 1,000 or at least 10,000) images of an ocular surface from, e.g., a population of subjects. In various embodiments, a portion of the plurality of images of the ocular surface from the population of subjects includes images of micro-neuromas.

The invention further provides a non-transitory computer readable medium having instructions for analyzing an image of an ocular surface stored thereon, including: a) a neural network including: i) a pre-trained residual learning architecture comprising about 50 layers, where the residual learning architecture was pre-trained with an image database; ii) batch normalization; iii) Dropout regularization; and iv) data augmentation prior to analysis by the residual learning architecture, where the data augmentation includes at least one of data blending augmentation, e.g., mix-up or manifold mix-up, data interpolating augmentation, random image flipping, random image rotation, or random image crops; and b) a backpropagation algorithm including: i) stochastic gradient descent, wherein the stochastic gradient descent further comprises momentum gradient acceleration with a value of 0.9; and ii) a learning rate of 0.00001.

The invention additionally provides a method of identifying a micro-neuroma in an image of an ocular surface of a subject, including analyzing the image of the ocular surface of the subject using a non-transitory computer readable medium having instructions stored thereon as described herein.

The invention also provides methods of diagnosing NCP, the methods including detection of micro-neuromas on the ocular surface of the eye of a patient, e.g., as described herein, optionally in combination with one or more additional steps of clinical assessment.

In some embodiments, the methods further include the use of one or more of (i) symptom questionnaire(s), (ii) functional somatosensory testing (e.g., proparacaine challenge test, corneal esthesiometry, or other nerve function tests), (iii) clinical examination (e.g., assessment of signs of ocular surface disease), (iv) assessment of ocular co-morbidities (e.g., Meibomian gland dysfunction, ocular allergy, conjuctivochalasis, and/or recurrent erosion syndrome), and (v) assessment of nerve density and morphology (e.g., detection of neuromas, such as micro-neuromas).

In some embodiments, the assessment of nerve morphology comprises the detection of micro-neuromas, optionally using a system as described herein.

The invention also includes methods of determining the cause of contact lens discomfort in a subject, the methods including determining whether the cornea of the subject comprises one or more micro-neuromas. Optionally, the methods can include the use of a system and/or a transitory computer readable medium as described herein.

Also, the invention includes methods for determining whether a subject may be at risk of developing contact lens discomfort, the methods including determining whether the cornea of the subject comprises one or more micro-neuromas. Optionally, the methods can include the use of a system and/or a transitory computer readable medium as described herein.

Other features and advantages of the invention will be apparent from the following detailed description, the drawings, and the claims.

DETAILED DESCRIPTION

The invention provides methods and systems for diagnosing neuropathic corneal pain and the basis thereof. In some embodiments, the methods of the invention involve detection of neuromas (e.g., micro-neuromas) on patient corneas, wherein detection of the neuromas (e.g., micro-neuromas) is an indication that the patient has neuropathic corneal pain (NCP), rather than (or in addition to) a different condition (e.g., dry eye disease; also see below). As explained further below, this detection method is optionally used in combination with one or more other methods, as described herein (e.g., assessment of symptoms of eye discomfort; also see below). The methods of the invention can, in some embodiments, be carried out using systems including AI features, such as neural networks (e.g., as described herein).

In some embodiments, the invention provides methods in which NCP is assessed by steps including, e.g., (i) symptom questionnaire(s), (ii) functional somatosensory testing (e.g., proparacaine challenge test, corneal esthesiometry, or other nerve function tests), (iii) clinical examination (e.g., assessment of signs of ocular surface disease), (iv) assessment of ocular co-morbidities (e.g., Meibomian gland dysfunction, ocular allergy, conjuctivochalasis, and/or recurrent erosion syndrome), and (v) assessment of nerve density and morphology (e.g., detection of neuromas, such as micro-neuromas), e.g., as described herein. Optionally, detection of neuromas (such as micro-neuromas) can be carried out using the systems and methods described herein (e.g., AI systems including neural networks). The methods can include all of the five steps listed above or various subsets of, e.g., 1, 2, 3, or 4 of these steps, with all possible combinations of the steps (and the sub-parts thereof) being contemplated as being within the scope of the invention. Reference is made to Dieckmann et al., Ophthalmology, 2017: 1-14, in regard to specific features of some of these methods.

The invention also includes methods of determining the cause of contact lens discomfort in a subject, the methods including determining whether the cornea of the subject comprises one or more micro-neuromas. Also, the invention includes methods for determining whether a subject may be at risk of developing contact lens discomfort, the methods including determining whether the cornea of the subject comprises one or more micro-neuromas. Optionally, these methods can include the use of a system and/or a transitory computer readable medium as described herein.

Figure 1A:
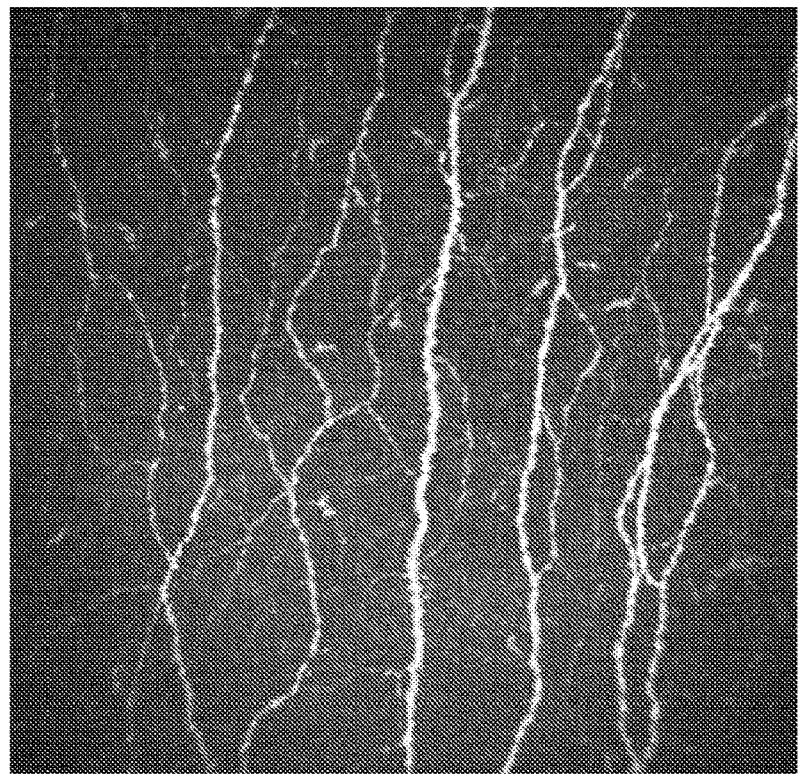
FIGS. 1A and 1B: In vivo confocal microscope images of healthy subbasal nerves without micro-neuromas (FIG. 1A) and diseased subbasal nerves showing the presence of micro-neuromas (FIG. 1B). The micro-neuromas in FIG. 1B are indicated by the arrows.
Figure 1B:
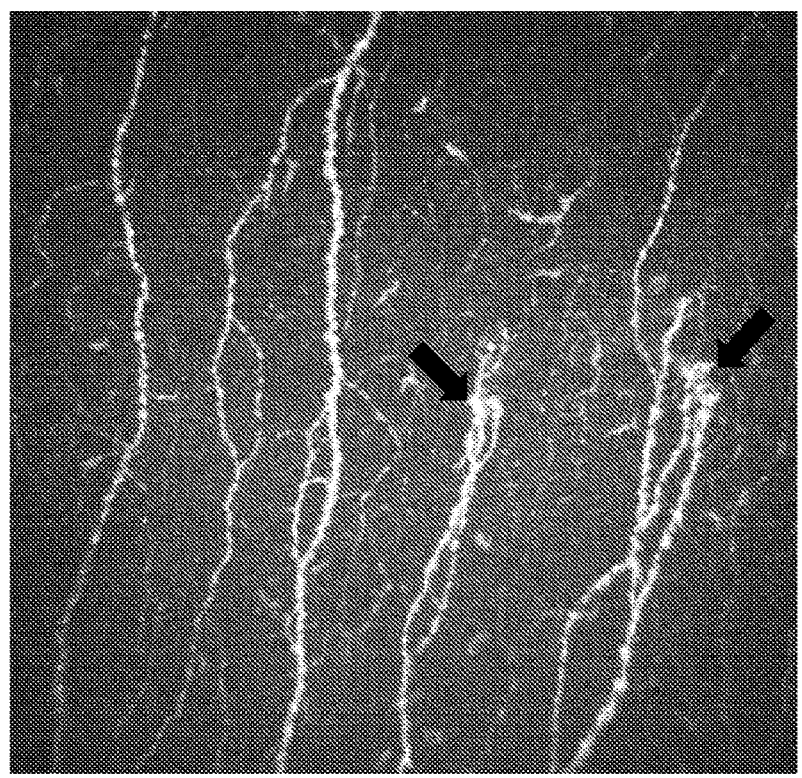

The present invention further provides a system for determining the presence of a tissue growth on the surface of a nerve, e.g., a neuroma, such as a micro-neuroma, from an in vivo captured image of a tissue surface, e.g., the ocular surface, such as the corneal surface. Exemplary images of healthy corneal tissue and diseased corneal tissue showing micro-neuromas are shown in FIGS. 1A and 1B, respectively. This information can then be used for differentially diagnosing neuropathic corneal pain. An advantage of the system is that it allows for the automated processing of acquired eye images using a pre-trained neural network algorithm.

The systems include two key components: an in vivo confocal microscope and a computer that is optionally connected to the in vivo confocal microscope and is configured to collect, store, and process the acquired image data. The system may be implemented in one or more parts. For example, the in vivo confocal microscope and the computer may be separate components, or they may be physically connected. When used as separate components, the computer, or a part of it, may be in a physically different location than the in vivo confocal microscope.

In Vivo Confocal Microscope

An in vivo confocal microscope is a non-invasive diagnostic imaging tool that enables a clinician to collect both morphological and quantitative information about a tissue surface, e.g., the ocular surface. In vivo confocal microscopy has high magnification, e.g., up to 800×, and high spatial resolution, e.g., up to 1 µm, to allow for precise imaging of detailed tissue structures. In addition, in vivo confocal microscopy further allows for depth profiling of a tissue surface, e.g., the ocular surface, such that structures below the outermost tissue surface can be imaged and analyzed. For example, in vivo confocal microscopy can be utilized to image the cornea to measure nerve density, nerve tortuosity, nerve thickness, or nerve beading.

In general, an in vivo confocal microscope uses a series of pinhole apertures and focusing elements, e.g., lenses, within the microscope objective to direct a light beam from a coherent light source, e.g. a laser, such as a diode laser, onto a small spot on the ocular surface and collect the light that reflects back from that small spot on the ocular surface. The microscope objective can then be moved in the three dimensional plane to image the entirety of the ocular surface. In vivo confocal microscopes are further able to collect many images per scan at every spatial point, increasing the information content provided to the clinician.

Exemplary in vivo confocal microscopes include the Nidek Confoscan Series microscopes and the Heidelberg Retina Tomograph II (HRT-II) equipped with the Rostock Cornea Module.

Computer

The data produced by the in vivo confocal microscope may be sent to a computer for processing and displaying the processed data to the user. The computer may receive the data from the in vivo confocal microscope's light detector, e.g., a photomultiplier tube, by way of a physical connection, such as a USB cable or similar hardware connection, e.g., the computer is directly incorporated into the in vivo confocal microscope. Alternatively or additionally, the data from in vivo confocal microscope may be sent to the computer via a wireless connection, such as an optical, RF, or other wireless connection, e.g., Bluetooth. In some cases, the data from the in vivo confocal microscope is communicated to the computer by remote access, e.g., via a cloud server accessible through the internet. The computer system is programmed to process the data and provide the image of the tissue surface, e.g., the ocular surface, to the user. Programming may be via software, hardware, or a combination thereof. For example, software can include microcode, assembly language code, a higher-level language code, or the like. Such software code can include computer readable instructions for performing various methods.

The software code may form portions of computer program products. Further, in an example, the software code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like. In another embodiment of present disclosure, a computer readable storing medium may be provided with computer executable instructions stored thereon. The data from the in vivo confocal microscope may be processed by a single program. Additionally or alternatively, multiple computer programs may be used in processing the data.

Neural Network

An aspect of the present application is directed to a non-transitory computer readable medium having instructions stored thereon, wherein the instructions, when executed by a processor, perform a method for automatically determining the presence of at least one neuroma on a plurality of images of an ocular surface of a patient. The non-transitory computer readable medium, and thus the computer may include a neural network for processing the signal from the in vivo confocal microscope. Neural networks are patterned mathematically to acquire, process, and interpret incoming information in a manner similar to the human brain, e.g., by taking input information and passing it along to at least one "neuron," further propagating information until terminating at an output. By passing information along to multiple "neurons" the neural network is able to improve the way in which it interprets an input signal, i.e., it learns from previous input signals, thereby improving the accuracy of the end result. The "neurons" are typically organized in layers. Different layers may perform different kinds of transformations on their inputs. Signals travel from the first (input), to the last (output) layer, possibly after traversing the layers multiple times, with each layer performing a mathematical manipulation on the data. The data from the output node is then provided to the end user on a display, such as a computer monitor or mobile device, such as a laptop computer display, tablet, or cellular telephone.

In order for a program such as a neural network to be able to learn from input data and output an appropriate solution to a problem, it first is trained using images that provide an initial set of conditions which represents a correct value or series of values for a problem to be iteratively solved. The training data provides a probabilistic value for the "correct" value of a given problem at each input value. In some embodiments, the neural network may be pre-trained with a generic set of images before further training with exemplary images of micro-neuromas; this is known as transfer learning. For example, a neural network may be pre-trained by using an image database, e.g., ImageNet, containing millions of images of everyday objects, e.g., animals, fruit, etc., in order to define a preliminary set of statistical weights for the neural network. Alternatively, or in addition, the neural network may be trained using a publically available medical image database, e.g., the U.S. National Institute of Health (NIH) Clinical Center Chest X-Ray database. The training set data may further include images of micro-neuromas identified by a trained professional, e.g., an ophthalmologist. The physical characteristics of the identified micro-neuromas may be used to provide probabilistic conditions of what the "ideal" micro-neuroma should look like when compared to the structures of healthy nerves, e.g., nerves that do not contain a micro-neuroma. In some cases, the training set for the neural network includes images of both healthy corneal tissue and diseased corneal tissue, e.g., images of corneal tissue containing at least one micro-neuroma, collected from a population of subjects. Independent of the specific training set, the training set data then provides further refinement of the statistical weights of the neural network. These probabilistic conditions, known as statistical weights, may be adjusted each time the neural network attempts to identify a micro-neuroma in an image, and training the neural network may include analyzing each image in a set of images multiple times, e.g., 2, 3, 4, or more, to continually update the statistical weights. Each iteration of image analysis improves the statistical weights, and thus the ability of the neural network to correctly identify a particular feature of an image, e.g., identify a micro-neuroma, in an image collected by an in vivo confocal microscope.

In general, updating the statistical weights in the neural network can be achieved using the backwards propagation of errors, i.e., backpropagation, by calculating the gradient of a loss function, e.g., an error function. This is effectively an optimization or minimization problem, as the goal of the neural network is to have the smallest possible errors, and backpropagation is achieved by an algorithm to find the set of statistical weights that minimizes the error. Optimization algorithms suitable for use in a neural network of the invention include, but are not limited to, gradient descent, e.g., stochastic gradient descent (SGD), SGD with momentum gradient acceleration, i.e., "momentum," or SGD with Nesterov momentum, RMSprop, adaptive gradient (AdaGrad), ADADELTA, adaptive moment estimation (Adam) and its variants, e.g., AdaMax and Nadam, and variations and combinations thereof. Momentum gradient acceleration, as used within the context of neural networks of the present invention, is a minimization scheme where the update to the gradient is remembered and used in a linear combination with the gradient to determine the next iterative update to the gradient while preventing oscillating of the gradient in a local minimum. In this configuration, the addition of momentum gradient acceleration helps accelerate gradient vectors in the right directions, thus leading to faster converging of the model. The momentum typically has a value from 0 to about 1, e.g., about 0.05, about 0.1, about 0.15, about 0.2, about 0.25, about 0.3, about 0.35, about 0.4, about 0.45, about 0.5, about 0.55, about 0.6, about 0.65, about 0.7, about 0.75, about 0.8, about 0.85, about 0.9, about 0.95, or about 1, with about being defined as +/−10% of a recited value. An exemplary optimization algorithm for a neural network of the present invention is SGD with a momentum of 0.9.

The updating of the statistical weights of the neural network is a function of both the optimization algorithm used for backpropagation as described herein, which controls the gradient, and how new statistical weights are used to override the existing statistical weights in the neural network. The parameter that controls data overriding is called the learning rate, and its magnitude represents the balance between precision and time. In general, a small learning rate increases the accuracy of the resulting statistical weights, but also increases the time of the calculation and may increase the change of getting stuck in a local minimum within the dataset. In contrast, a large value for the learning rate typically results in fast convergence, but reduces the accuracy of the calculation. As it applied to the present invention, the learning rate controls how much each update (e.g., the neural network analyzing an image) changes the neural network's statistical weights. The learning rate may be form about 0.000001 to about 0.1, e.g., from about 0.000001 to about 0.00001, about 0.000005 to about 0.00005, about 0.00001 to about 0.0001, about 0.00005 to about 0.0005, about 0.0001 to about 0.001, about 0.0005 to about 0.005, about 0.001 to about 0.01, about 0.005 to about 0.05, or about 0.01 to about 0.1, e.g., about 0.000001, about 0.000002, about 0.000003, about 0.000004, about 0.000005, about 0.000006, about 0.000007, about 0.000008, about 0.000009, about 0.00001, about 0.00002, about 0.00003, about 0.00004, about 0.00005, about 0.00006, about 0.00007, about 0.00008, about 0.00009, about 0.0001, about 0.0002, about 0.0003, about 0.0004, about 0.0005, about 0.0006, about 0.0007, about 0.0008, about 0.0009, about 0.001, about 0.002, about 0.003, about 0.004, about 0.005, about 0.006, about 0.007, about 0.008, about 0.009, about 0.01, about 0.02, about 0.03, about 0.04, about 0.05, about 0.06, about 0.07, about 0.08, about 0.09, or about 0.1, with about being defined as +/−10% of a recited value.

An exemplary learning rate for a neural network of the invention is 0.00001 For a neural network of the present invention, the images of healthy corneal tissue and diseased corneal tissue, e.g., images of corneal tissue containing at least one micro-neuroma, are represented by a series of numbers in a large matrix; these numbers represent pixel intensities of each pixel in the image. In some cases, the images used to train the neural network are unaltered, e.g., original, images from the medical imaging device, e.g., the in vivo confocal microscope, e.g., at native resolution.

Alternatively, the images that are used as input for the neural network may be resized for compatibility with the neural network. For example, in the present invention, images may be reduced in size, e.g., to a size of 240×240 pixels or 256×256 pixels, relative to the original images from the in vivo confocal microscope. The neural network may be configured to accept color images as input, e.g., where each pixel has a numerical value for the red, blue, and green (RGB) color channel. Alternatively, the neural network may be configured to accept grayscale images as input. Many neural networks, such as those utilized in the present invention, are not directly configured to accept grayscale images as input, and thus some manipulation of the grayscale input data is necessary for compatibility. For example, a grayscale image having a single color value at every pixel may have its single pixel color value mapped to each of the three color channels, e.g., the R, G, and B channels, of a neural network that accepts color images as input.

In some cases, the data that is to be used to train the neural network, e.g., information content extracted from a set of images, may be first pre-processed in order to ensure compatibility with the neural network's mathematical framework and to examine variability within the data set. The training set data, e.g., pixel intensity values, may be pre-processed using Z-scoring, e.g., subtracting the mean and dividing by the standard deviation of each data point, normalization, e.g., histogram or contrast normalization, imputation of missing values, principal component analysis (PCA), or whitening. Other pre-processing algorithms are known in the art. Key to the performance of the neural network is to minimize the amount of pre-processing that is applied to the data, as neural networks typically learn more efficiently using data that has been minimally processed.

In some cases, the data that is to be used to train the neural network may be augmented to enhance the performance, e.g., accuracy, of the neural network. This data augmentation may be achieved by altering one or more properties of the image and then providing the neural network the altered images. This has the effect of artificially increasing the number of data points that are part of the neural network's training set, as each of the altered images is treated as new input data, distinct from any other data point even though the source of the data may be the same image. The physical properties of an image that may be altered include, but are not limited to, randomly flipping the image on one or more of the coordinate axes, e.g., the x- or y-axis, randomly rotating the image, randomly cropping the image, randomly stretching the image, randomly zooming in on the image, a mixup image augmentation and its variants, e.g., manifold mixup, or a combination thereof. Mixup image augmentation, as used in the context of the present invention, is a type of data interpolation scheme in which a composite image is created from two (or more) random images from the data set. The neural network is told the "correct" answer, e.g., that the image is a composite of two or more images, and the image is delivered to the neural network to evaluate whether or not it can arrive at the correct answer. Exemplary image alterations are random flips, random crops, random rotations, and mixup image augmentation.

In general, the accuracy of a neural network is linearly correlated with the number of data points, e.g. number of images, used to train the neural network. In some cases, the number of images used to train the neural network is at least 1,000 images, e.g., at least 1,500 images, at least 2,000 images, at least 2,500 images, at least 3,000 images, at least 3,500 images, at least 4,000 images, at least 4,500 images, at least 5,000 images, at least 5,500 images, at least 6,000 images, at least 6,500 images, at least 7,000 images, at least 7,500 images, at least 8,000 images, at least 8,500 images, at least 9,000 images, at least 9,500 images, at least 10,000 images, at least 10,500 images, at least 11,000 images, at least 11,500 images, at least 12,000 images, at least 12,500 images, at least 13,000 images, at least 13,500 images, at least 14,000 images, at least 14,500 images, or at least 15,000 images. In particular embodiments, the number of images used to train the neural network is at least 10,000 images, e.g., at least 10,000 images, at least 11,000 images at least 12,000 images, at least 13,000 images, at least 14,000 images, at least 15,000 images, at least 16,000 images, at least 17,000 images, at least 18,000 images, at least 19,000 images, at least 20,000 images, or more.

Figure 2:
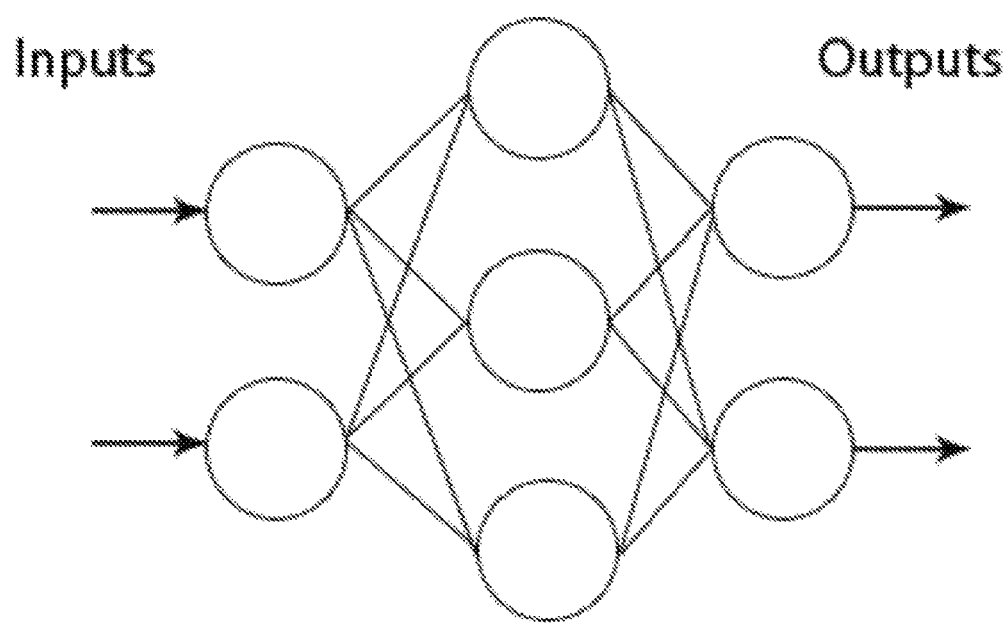
FIG. 2: General architecture of a feedforward neural network showing input nodes, hidden nodes, and output nodes.

A neural network of a system of the invention may be arranged into three components: the input layer, the hidden layer or layers, and the output layer. In particular, the neural network may be a convolutional neural network, which is a neural network that can manipulate three dimensional data and returns three dimensional data as output. An example architecture of a standard neural network is shown in FIG. 2. Each of the layers is divided into sub-units called nodes. Within the input, each of the nodes corresponds to a single datum point derived from the images collected by the in vivo confocal microscope. The single datum point in each input node is then duplicated and placed into every node in the first of the hidden layers; this type data passing is known as feedforward, as each input node is independent of the other input nodes in the input layer. In some cases, the layers of the network may normalize the data in the layer to improve the network training process. This normalization of the layer data may be achieved by batch normalization, group normalization, instance normalization, or a combination of normalization schemes. An exemplary in-layer normalization scheme is batch normalization.

The neural network contains at least one hidden layer and may contain others. The neural network may contain, for example, anywhere from 2 to 100 hidden layers, e.g., from 2 hidden layers to 20 hidden layers, from 10 hidden layers to 30 hidden layers, from 20 hidden layers to 40 hidden layers, from 30 hidden layers to 50 hidden layers, from 40 hidden layers to 60 hidden layers, from 50 hidden layers to 70 hidden layers, from 60 hidden layers to 80 hidden layers, from 70 hidden layers to 90 hidden layers, or from 80 hidden layers to 100 hidden layers, e.g., 2 hidden layers, 3 hidden layers, 4 hidden layers, 5 hidden layers, 6 hidden layers, 7 hidden layers, 8 hidden layers, 9 hidden layers, 10 hidden layers, 15 hidden layers, 20 hidden layers, 25 hidden layers, 30 hidden layers, 35 hidden layers, 40 hidden layers, 45 hidden layers, 50 hidden layers, 55 hidden layers, 60 hidden layers, 65 hidden layers, 70 hidden layers, 75 hidden layers, 80 hidden layers, 85 hidden layers, 90 hidden layers, 95 hidden layers, or 100 hidden layers.

In some cases, the total number of layers, including the input, output, and hidden layers, of the neural network may be from 3 to 102 layers, e.g., from 3 layers to 20 layers, from 10 layers to 30 layers, from 20 layers to 40 layers, from 30 layers to 50 layers, from 40 layers to 60 layers, from 50 layers to 70 layers, from 60 layers to 80 layers, from 70 layers to 90 layers, or from 80 layers to 102 layers, e.g., 2 layers, 4 layers, 6 layers, 8 layers, 10 layers, 12 layers, 14 layers, 16 layers, 18 layers, 20 layers, 22 layers, 24 layers, 26 layers, 28 layers, 30 layers, 32 layers, 34 layers, 36 layers, 38 layers, 40 layers, 42 layers, 44 layers, 46 layers, 48 layers, 50 layers, 52 layers, 54 layers, 56 layers, 58 layers, 60 layers, 62 layers, 64 layers, 66 layers, 68 layers, 70 layers, 72 layers, 74 layers, 76 layers, 78 layers, 80 layers, 82 layers, 84 layers, 86 layers, 88 layers, 90 layers, 92 layers, 94 layers, 96 layers, 98 layers, 100 layers, or 102 layers.

The number of hidden layers is often linearly correlated with the accuracy and learning ability of the neural network—as the number of hidden layers increases, so too does the accuracy of the resulting output variable, e.g., the correct identification of a micro-neuroma present on the ocular surface, to a certain limit where oversaturation may occur. Each layer consists of a number of individual nodes for receiving data from the previous layer, be it the input layer or another hidden layer within in the neural network. The nodes of the hidden layers contain the probabilistic conditions, e.g., values from 0 to 1, for what the "ideal" micro-neuroma looks like relative to a healthy nerve. Each node within the hidden layer receives every data point from the previous layer, i.e., the data point from a single node is copied and placed into every node in the next layer of the neural network.

In the hidden layers of the neural network of the invention, the images collected from the in vivo confocal microscope are processed to generate a numerical representation of the features of said image, e.g., size, shape, color, etc. This set of numerical representations is normalized to produce a series of input values between 0 and 1, with the input data for each node further including the correct answer for identifying a micro-neuroma, e.g., a probability of 1. These normalized values are then used as input for the activation function of the neural network, which is a linear or non-linear function used to simulate the learning ability of biological neurons. For neural networks of the invention, this function is non-linear, e.g., a sigmoidal function, such as, a hyperbolic tangent or logistic function, as it has an easily computable derivative; this type of neural network is known as a multilayer perceptron. The first derivative is used to calculate the error of the neural network for improving the learning ability by updating the statistical weights. The single value, e.g., datum point, in each input node is directed to a sigmoidal activation function in each input node, returning a single value. This results in a single value for each node in the hidden layer, and each of these datum points is copied and sent as input to every node in the next hidden layer, with every node receiving as input all data from the previous layers' nodes. The process of passing through the sigmoidal activation function, and passing to the next layer's nodes is repeated for each of the hidden layers of the neural network. The final step in using a neural network of the invention is to pass the data from the final layer of hidden nodes into the nodes of the output layer, which includes a final round of passing it through the sigmoidal activation function to produce a single output for each output node. This output, when un-normalized, returns the presence of a micro-neuroma in the image of the ocular surface. Alternatively, the neural network may be a residual neural network, where layers are "skipped" by the subtractions of a feature identified from one or more previous layers in the neural network. This has the advantage of allowing for an increase number of layers without loss of accuracy and facilities easier training of the neural network.

Exemplary neural network architectures that are suitable for use in the present invention include, but are not limited to, VGG, e.g., VGG-16, VGG-19, or variants, residual learning architectures, e.g., ResNet, e.g., ResNet-50, ResNet-101, ResNet-152, or variants, Inception, e.g., Inception-V1, Inception-V2, Inception-V3, or variants, Densenet and variants, Xception and variants, Vception and variants. NasNet and variants, MobileNet and variants, and any combination thereof. An exemplary neural network architecture is the residual-based neural network ResNet-50, where the 50 indicates that the ResNet has a 50-layer architecture.

A key feature of a neural network is its ability to extract generalizable principles from the data and improve the statistical weights to increase the accuracy of the model. However, neural networks may overfit their statistical weights by attempting to characterize noise in the dataset as data, e.g., the neural network is "memorizing" the data from a training set. In order to prevent the neural network from overfitting, the neural network needs to be regularized, e.g., decreasing the importance of higher order terms in the calculation of the error in updating the statistical weights. Examples of regularization schemes useful for a neural network of the present invention include, but are not limited to, L1, e.g., LASSO, regression, L2, e.g., Ridge, regression, Dropout, or drop connect. Other regularization schemes are known in the art. An exemplary regularization scheme for a neural network of the present invention is Dropout.

Data Display

Once the data has been processed by the computer, e.g., programmed with a neural network, the data is displayed to the user. The data display can be, e.g., a wired device, such as a computer monitor, or can be a wireless device, e.g., a cellular telephone or a tablet.

Figure 3A:
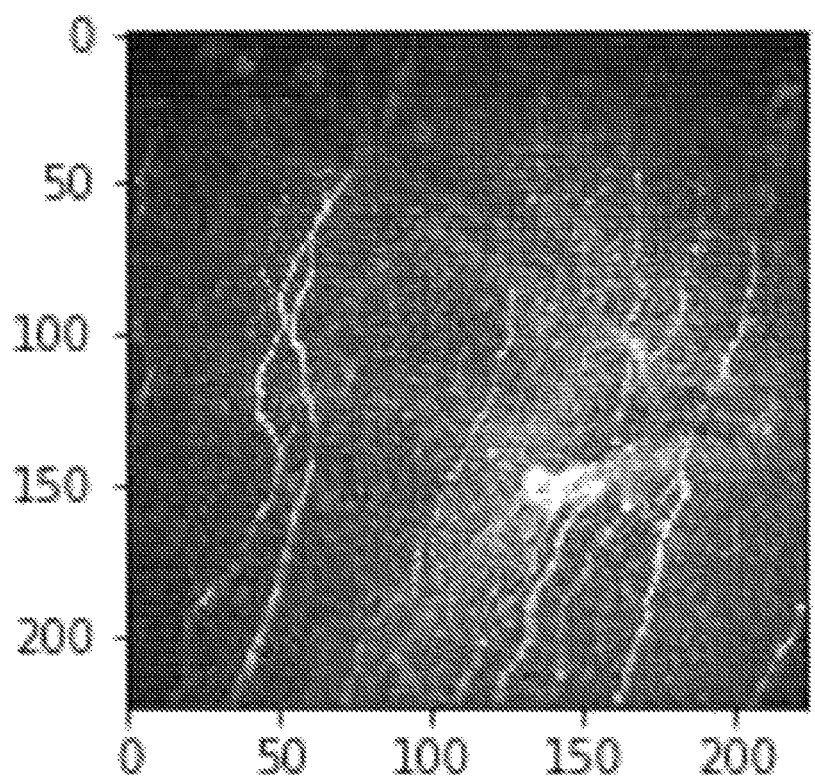
FIGS. 3A and 3B: Image of a micro-neuroma (FIG. 3A) and the false color "heat map" of the same image (FIG. 3B) highlighting the region of interest identified by the neural network used in the system of the invention. Darker colors are low probability of a micro-neuroma and lighter colors are high probability of a micro-neuroma.
Figure 3B:
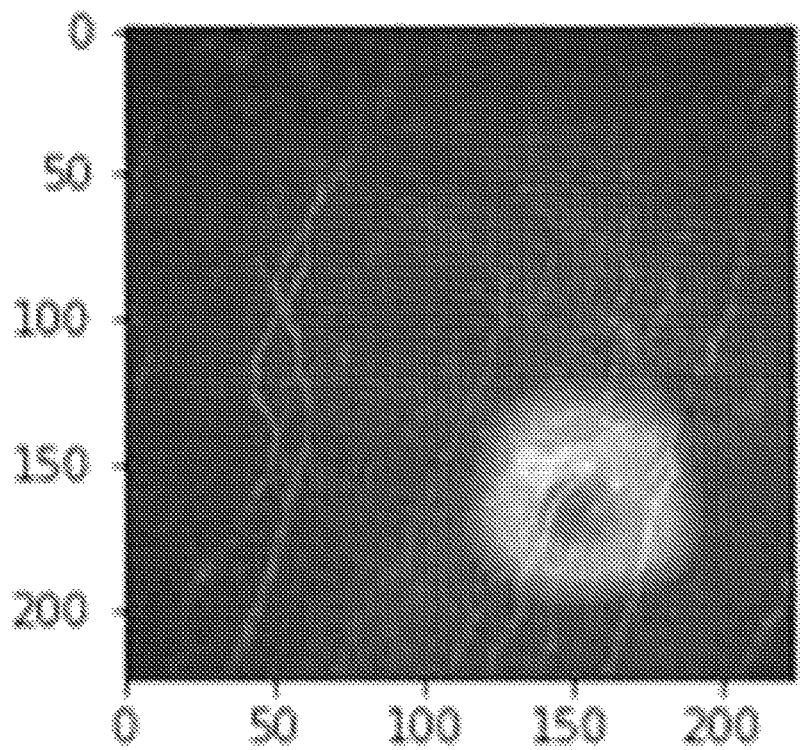

The output data from a neural network useful for a system of the invention returns the probability that the acquired image contains a neuroma, e.g., a micro-neuroma, on the ocular surface. This data is numerical, and in practice returns a binary answer of "yes" or "no" that a micro-neuroma is present on the ocular surface. In order to visualize the resulting output of the neural network, the output data can be manipulated using 3D plotting software in order to generate a false color "heat map" of the location of the micro-neuroma. An example of this is shown in FIGS. 3A and 3B, where the original image (FIG. 3A) and the heat map image (FIG. 3B) indicates the region of interest identified by the neural network for the image of FIG. 3A.

Methods

The invention features methods of identifying the presence of a neuroma, such as a micro-neuroma, on an ocular surface or within an ocular tissue (e.g., the cornea). In the methods, light from the light source of an in vivo confocal microscope is directed onto the ocular surface of the subject to produce an image of at least a portion of the ocular surface. The collected image is sent to a computer programmed with a neural network that uses the information in the collected image to determine the presence of a neuroma, such as a micro-neuroma. After processing, the image is displayed to the user, typically along with the results of the neural network analysis, which as discussed above, are probabilities that a neuroma, such as a micro-neuroma is present in the image. The data from the neural network can also be processed into a false color "heat map" that presents a pictorial representation of the neural network data for identifying regions of interest in the image.

The invention further provides methods of differentially diagnosing neuropathic corneal pain from other related ocular indications in a subject. In the methods, an image of at least a portion of the ocular surface is acquired using a suitable imaging technique, e.g., in vivo confocal microscopy. The image is sent to a computer that is programmed with a program configured to analyze the image. The results of this analysis as well as the captured image of the ocular surface are then displayed to the user. The analysis is configured to indicate if there is an anatomical structure present on the ocular surface, such as a neuroma, e.g., a micro-neuroma, that may be a marker for neuropathic corneal pain.

Neuropathic corneal pain may be a standalone ocular indication or may be co-existent with other related ocular indications. Thus, providing proper treatment of neuropathic corneal pain is keyed on the ability to correctly identify it from other related ocular indications that may exhibit similar pathologies. For example, a subject may experience neuropathic corneal pain and dry eye disease (DED) concurrently, but neuropathic corneal pain can be differentiated from dry eye disease by the presence of micro-neuromas on the corneal surface. Other related ocular indications include, but are not limited to dry eye disease, complications from refractive surgery, Sjögren's Syndrome, neuralgia associated with herpes viruses, chemical irritations, side effects of pharmaceuticals, chemotherapy, and radiation therapy. Thus, an advantage of the invention is the ability to use in vivo confocal microscopy and rapid image analysis with a neural network to both differentiate cause of symptoms (neuropathic corneal pain relative to other related ocular indications) and to determine if neuropathic corneal pain is present concurrently with other diagnosed ocular or non-ocular conditions. For example, a slit-lamp examination using ocular dyes, such as fluorescein, rose bengal, and lissamine green, can reveal the presence of corneal epithelial breakdown or a devitalized cornea consistent with DED, but cannot visualize the nerves of the cornea to determine the presence of micro-neuromas consistent with neuropathic corneal pain. Furthermore, a method of the invention may be useful for subject stratification, e.g., to include or exclude patients with standalone neuropathic corneal pain or neuropathic corneal pain concurrent with other indications, for trials, e.g., clinical trials, to either have subject groups containing solely subjects with standalone neuropathic corneal pain for trials or to include those subject with concurrent ocular indications to assess subgroup analysis.

In some cases, the method further includes the administration of a therapeutic agent suitable for treating neuropathic corneal pain. As root causes of neuropathic corneal pain include injured nerves and inflammation of the ocular surface, therapeutic treatments include both orally- and parenterally-, e.g., topically-, administered therapeutics to help reduce the inflammation and/or pain. Examples of oral therapeutics useful for treating neuropathic corneal pain include, but are not limited to, tricyclic antidepressants, e.g., nortriptyline and amitriptyline, anticonvulsants, e.g., gabapentin, pregabalin, carbamazepine, or duloxetine, opioid antagonists, opioid agonists, GABA inhibitors, serotonin-norepinephrine reuptake inhibitors, transient receptor potential vanilloid (TRPV) receptor antagonists, transient receptor potential melastatin (TRPM) receptor antagonists, and sodium channel blockers. For example, the tricyclic antidepressant nortriptyline has been shown to have a strong effect on reducing neuropathic corneal pain in subjects with micro-neuromas present on the ocular surface. In other cases, the therapeutic treatment for neuropathic corneal pain may include parenterally-, e.g., topically-, administered therapeutics for both neuronal and ocular surface regeneration while alleviating symptoms. Examples of parenterally-administered therapeutics useful for treating neuropathic corneal pain include, but are not limited to, tricyclic antidepressants, e.g., nortriptyline and amitriptyline, anticonvulsants, e.g., gabapentin, pregabalin, carbamazepine, or duloxetine, autologous serum tears, corticosteroids, cryopreserved amniotic membranes, amniotic fluid, protective contact lenses, scleral lenses, and artificial tears.

In addition to managing and treating the pain associated with neuropathic corneal pain, the methods may further include at least one parallel diagnosis test to further aid a clinician in properly diagnosing neuropathic corneal pain. Parallel diagnosis tests include, but are not limited to, ocular pain questionnaires, functional somatosensory testing, and physical eye examinations. Ocular pain questionnaires useful for the present invention include the Ocular Surface Disease Index (OSDI), the McMonnies Dry Eye Questionnaire, the Standardized Patient Evaluation for Eye Dryness, the National Eye Institute Vision Function Questionnaire, the Symptom Assessment in Dry Eye, and the Ocular Pain Assessment Survey (OPAS). Functional somatosensory testing is useful for correctly establishing the origin of neuropathic corneal pain and a proper treatment strategy. Functional somatosensory tests useful for a method of the invention include the proparacaine challenge test and direct somatosensory measurement with an ocular esthesiometer, e.g., an "air puff" test for evaluating the mechanical response to stimuli. A physical examination of the eye may include photographs of the eye with topically applied stains, e.g., fluorescein, measurement of tear film stability and volume, and tear osmolarity.

The invention further provides methods of assessing a treatment regimen for neuropathic corneal pain. In the methods, a first set of in vivo confocal microscopy images of an ocular surface of a subject experiencing neuropathic corneal pain is acquired and analyzed using a computer programmed with a neural network to identify at least one parameter, e.g., an anatomical structure, e.g., a micro-neuroma, associated with neuropathic corneal pain. The subject is then placed on a treatment regimen using a therapeutic agent suitable for treating neuropathic corneal pain for a fixed length of time. After the fixed length of time, a second set of in vivo confocal microscopy images of the ocular surface of the subject experiencing neuropathic corneal pain is acquired and analyzed using a computer programmed with a neural network as described herein to determine structural changes in the anatomical structure, e.g., a micro-neuroma, causing neuropathic corneal pain. The steps of therapeutic treatment and re-imaging of the ocular surface are repeated until the subject experiences a reduction, or the elimination, of neuropathic corneal pain, with the reduction of neuropathic pain being a result of a reduction in at least one dimension of the anatomical structure, e.g., a micro-neuroma, identified by the in vivo confocal microscopy imaging.

In some cases, the therapeutically sufficient duration, e.g., the time between imaging studies (during which therapeutic treatments are administered), may be at least 2 weeks, e.g., at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 17 weeks, at least 18 weeks, at least 19 weeks, at least 20 weeks, or more. The duration of imaging and therapeutic treatment is determined by the reduction of size of micro-neuromas causing neuropathic corneal pain and the rate of this reduction. As the micro-neuroma decreases in size, with a concurrent decrease in felt neuropathic corneal pain, the fixed length of time between imaging studies may be increased.

The invention further provides a method of determining the efficacy of a treatment for neuropathic corneal pain. In the method, a subject is diagnosed with having or potentially having neuropathic corneal pain and a first set of in vivo confocal microscopy images of an ocular surface of a subject experiencing neuropathic corneal pain is acquired and analyzed using a computer programmed with a neural network to identify an anatomical structure, e.g., a micro-neuroma, causing neuropathic corneal pain. After the first set of imaging, the subject is then administered a therapeutic agent. After administration of the therapeutic agent, a second set of in vivo confocal microscopy images of the ocular surface of the subject experiencing neuropathic corneal pain is acquired and analyzed using a computer programmed with a neural network to a change in the at least one parameter associated with neuropathic corneal pain, e.g., dimension changes in a micro-neuroma. The output indicative of the efficacy of the treatment for neuropathic corneal pain, such as the processed images from the neural network, are stored or provided to the user.

An exemplary use for a method of the invention is for evaluating the therapeutic response of novel therapeutic agents for treating neuropathic corneal pain during a longitudinal study, such as a clinical trial. Therapeutic agents currently undergoing development and clinical trials for neuropathic corneal pain include, but are not limited to, tricyclic antidepressants, anticonvulsants, nerve growth factors, naltrexone, e.g., topical naltrexone, amniotic membrane gel, cryopreserved amniotic membranes, amniotic fluid, dual enkephalinase inhibitors, Tivanisiran (Syl1001), anti-inflammatories (e.g., Loteprednol, cyclosporine, and lifitegrast), immunosuppressives, transient receptor potential vanilloid (TRPV) receptor antagonists, transient receptor potential melastatin (TRPM) receptor antagonists, and neuroregeneratives.

EXAMPLES

Example 1—Use of Neural Network to Detect Micro-Neuromas

In this example, a system of the invention was used to automate the detection of micro-neuromas on the ocular surface using data from a population of 15 patients. The ResNet-50 neural network, a deep learning neural network with over 24 million parameters and pre-trained using the ImageNet visual learning database, was used to automatically detect the presence or absence of micro-neuromas in validation images supplied to the neural network.

To further refine the pre-trained ResNet-50 neural network, a training set of in vivo confocal microscopy images was provided to the neural network to update the statistical weights. The total set of images contained 12,212 images from a diverse patient population suffering from dry eye disease (DED) and neuropathic corneal pain (NCP), corresponding to the data from 15 patients. The model was trained using 8 Titan X graphics processing units (GPUs) over a 24-hour period using a 12-patient training subset of the total set of images. To provide a comparison point and validation check of the model results, each of the training set images was categorized by a trained ophthalmologist as either containing a micro-neuroma or not containing a micro-neuroma. From this training set, 407 images (3.3%) were found to contain a micro-neuroma while 11,805 (96.7%) did not contain a micro-neuroma. The model was trained five separate times before being validated using the microscope images from the three patients who were not included in the training set. The set of validation images were run through the neural network five separate times to generate a sufficient set of results for statistical analyses.

Figure 4:
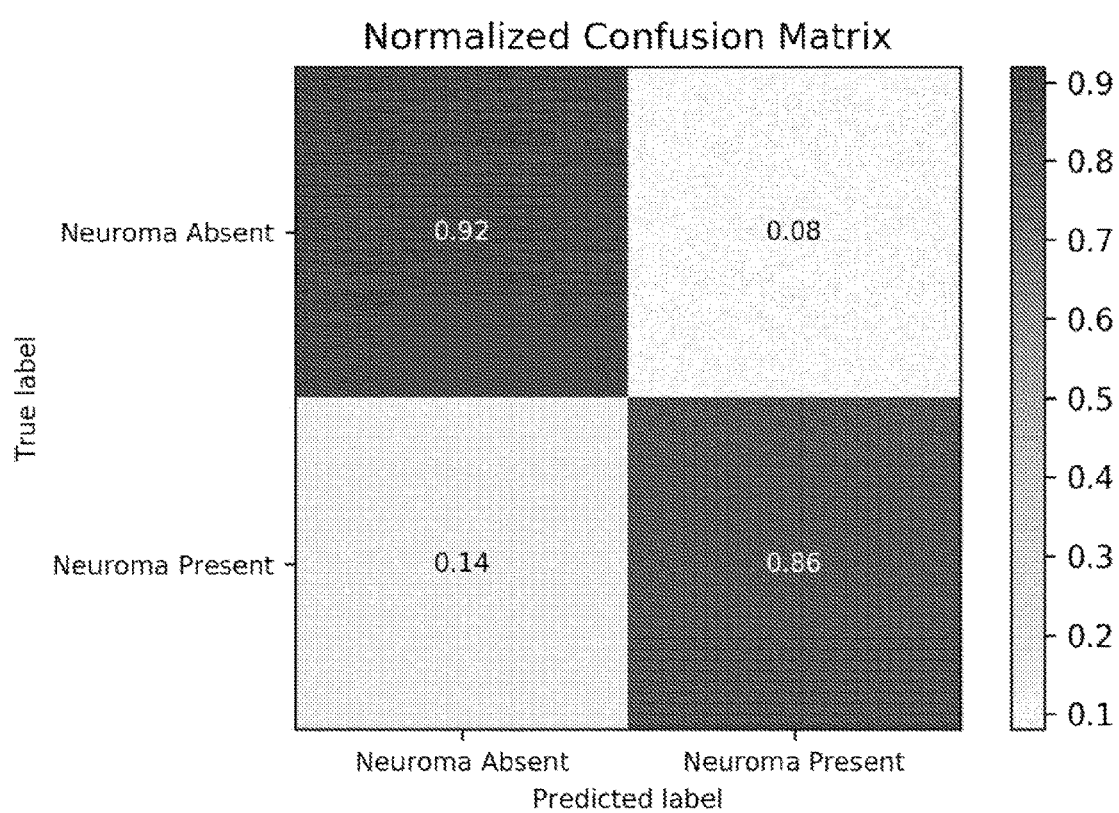
FIG. 4: Confusion matrix for the doubly trained neural network used to identify the images of a micro-neuroma in a set of validation images from a population of three patients.

FIG. 4 presents a normalized confusion matrix showing both how specific and sensitive the neural network was for identifying a micro-neuroma in the validation set of images. The y-axis of the matrix corresponds to the identified micro-neuroma classes (absent or present) identified by the trained ophthalmologist on the validation set and the x-axis of the matrix corresponds to the predicted micro-neuroma classes (absent or present) from the neural network. As is seen in the matrix, the neural network has a specificity, e.g., the probability that an image does not have a micro-neuroma, e.g., the ratio of the number of images without a micro-neuroma identified by the ophthalmologist to the sum of the number of images without a micro-neuroma identified by the ophthalmologist and the number of false positives identified by the neural network, of 0.92, e.g., 92%, indicating that the neural network performs well in not misidentifying the presence of a micro-neuroma in the validation set of images. The 95% confidence interval of the specificity was 0.91-0.95, with the specificity value form the neural network falling within the confidence interval. The matrix also indicates that the neural network has high sensitivity, e.g., the probability that an image has a micro-neuroma, e.g., the ratio of the number of images having micro-neuroma identified by the ophthalmologist to the sum of the number of images having a micro-neuroma identified by the ophthalmologist and the number of false negatives identified by the neural network, of 0.86, e.g., 86%, indicating that the model correctly identifies the majority of images that contain a micro-neuroma. The 95% confidence interval of the sensitivity was 0.54-0.87, with the sensitivity value form the neural network falling to the high side but within the confidence interval.

Figure 5:
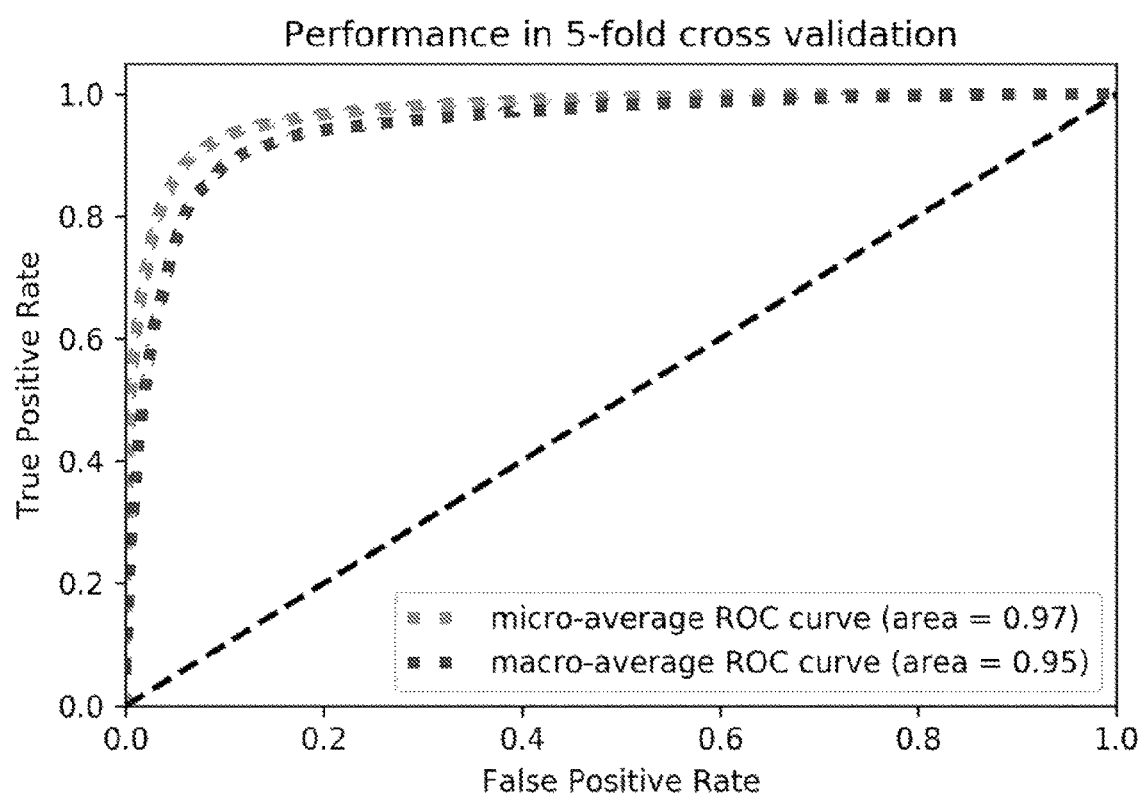
FIG. 5: Receiver operating characteristic (ROC) curve for the doubly trained neural network used to identify the images of a micro-neuroma in a set of validation images from a population of three patients.

FIG. 5 presents the results of a standard cross-validation scheme used to evaluate the performance of the neural network on validation set of images. The plot of FIG. 5 shows the true positive identification rate plotted against the false positive identification rate, e.g., the sensitivity vs. (1-specificity). The area under the curve (AUC) shown in FIG. 5, which is a metric for how the neural network identifies a positive feature, e.g., correctly identifies a micro-neuroma in the validation set, is 0.91, e.g., 91%, indicating strong performance of the neural network (noting that the 95% confidence interval for the AUC was 0.85-0.97).

In sum, the use of in vivo confocal microscopy image analyses is beneficial for the proper diagnosis of ocular surface diseases such as micro-neuromas. Current software used to identify micro-neuromas are not sufficient for analyses as they require manual intervention. We have shown that the identification of micro-neuromas in a patient population can be semi-automated by using artificial intelligence, e.g., a trained neural network, while maintaining a high degree of accuracy. This high degree of accuracy of the neural network allows for the standardization of in vivo confocal microscopy image analysis, thereby increasing the correct diagnosis of neuropathic corneal pain.

Example 2—Sensory Corneal Nerve Function Testing and Morphological Corneal Nerve Alterations In the experiments described in this Example, we investigated the morphological and functional corneal nerve changes as potential predictors of patient symptoms, with an emphasis on determining underlying structural abnormalities associated with contact lens discomfort.

Contact lens discomfort (CLD) is the leading cause for up to 51% of individuals to permanently discontinue contact lens-wear (CLW). Possible causative factors in the pathophysiology of CLD include mechanical forces from the contact lens, resulting in inflammation. The recent updated definition of dry eye disease (DED) by the dry eye workshop (DEWS)-II highlights the additional role of neurosensory abnormalities in the etiology of DED. Corneal nerve dysfunction is the pathophysiologic basis of many ocular surface diseases and disorders, including corneal neuralgia, neuropathy, contact lens discomfort, and neuropathic corneal pain (NCP). Neuropathic pain is defined as chronic pain caused by a lesion or disease of the somatosensory nervous system. Long-term injury to peripheral corneal sensory nerves leads to the development of ectopic activity and abnormal excitability of peripheral nerve terminals causing NCP.

Laser in vivo confocal microscopy (IVCM) is a non-invasive, high-resolution, real-time imaging technique, and allows layer-by-layer analysis of the corneal ultrastructure in ocular health and disease states, with images comparable to that of ex vivo histochemical techniques. Despite a growing body of research utilizing IVCM to investigate nerve and cellular changes in DED and ocular inflammation, there is paucity in understanding functional and morphological changes in CLD to date. Further, the potential role of neurosensory abnormalities in the etiology of CLD has not been studied to date.

Methods

For the assessment of the underlying structural abnormalities associated with contact lens wear, we performed a cross-sectional, controlled, single center study of 99 subjects. The subjects chosen for the single center study met the following minimum requirements:

18 years of age or older

No history of diabetes

No ocular surgery or ocular injury within the past year

No ocular infection within the past 3 months

No active ocular allergies

The 99-member subject pool were further subdivided into the following groups: normal control; asymptomatic contact lens wear (CLW); symptomatic contact lens wear (CLW); intolerant contact lens wear (CLW); and neuropathic corneal pain (NCP). The inclusion/exclusion criteria for each group is summarized in Table 1 below.

TABLE 1

Inclusion and Exclusion Criteria for the Four Subdivision Groups of the 99-member Subject Population.

| Group | Inclusion | Exclusion |
| --- | --- | --- |
| Normal Control | Clinical tests and eye exam align with normal ocular surface eye exam | Contact lens wear; Schirmer's <10 mm, TUBT <7, CFS >3/15, OSDI >12 |
| CLW: Asymptomatic | CLW >1 year & >10 hours daily; minimal discomfort in CLW; <14 CLDEQ-8 score | DED signs: Schirmer's <10 mm, TUBT <7, CFS >3/15, OSDI >12 |
| CLW: Symptomatic | CLW >1 year & <8 hours daily; discomfort in CLW; DED signs, ≥14 CLDEQ-8 score | No additional criteria |
| CLW: Intolerant/Lapsed | CLW >1 year & <6 hours of wear time or recently ceased due to symptoms of discomfort | DED signs: Schirmer's <10 mm, TUBT <7, CFS >3/15, OSDI >12 |

TABLE 1-continued

Inclusion and Exclusion Criteria for the Four Subdivision Groups of the 99-member Subject Population.

| Group | Inclusion | Exclusion |
|---|---|---|
| Neuropathic Corneal Pain | NCP diagnosed clinically and by IVCM | No additional criteria |

Clinical testing on the 99-member subject pool included: tear break-up time (TBUT), ocular staining (corneal fluorescein staining (CFS) and lissamine green staining (LGS)), and Schirmer's test, and pain and discomfort information was derived from visual analogues scale (VAS, 0-10) for pain and ocular surface disease index (OSDI). Corneal nerve function was assessed by response to topical 5% hypertonic saline (HS) and cold preservative free 0.9% normal saline (4° C.) using changes to VAS from baseline.

Figure 6A:
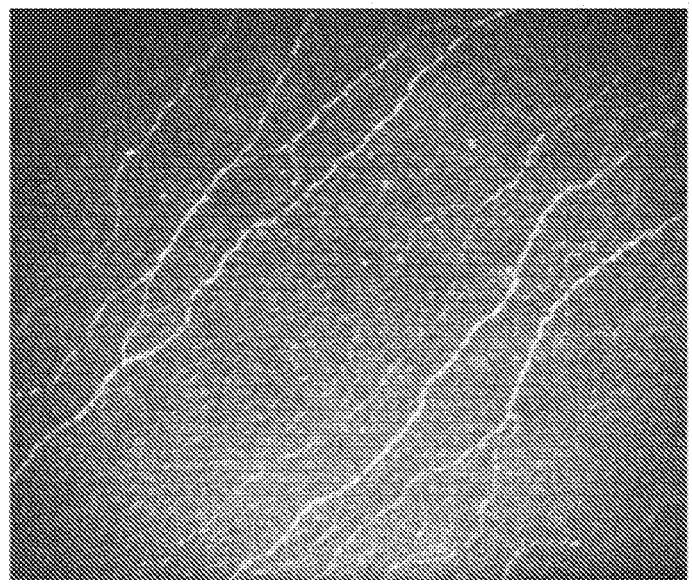
FIGS. 6A and 6B: Representative IVCM images of central corneas highlighting (FIG. 6A) normal and (FIG. 6B) altered nerve morphology (arrows: micro-neuromas).
Figure 6B:
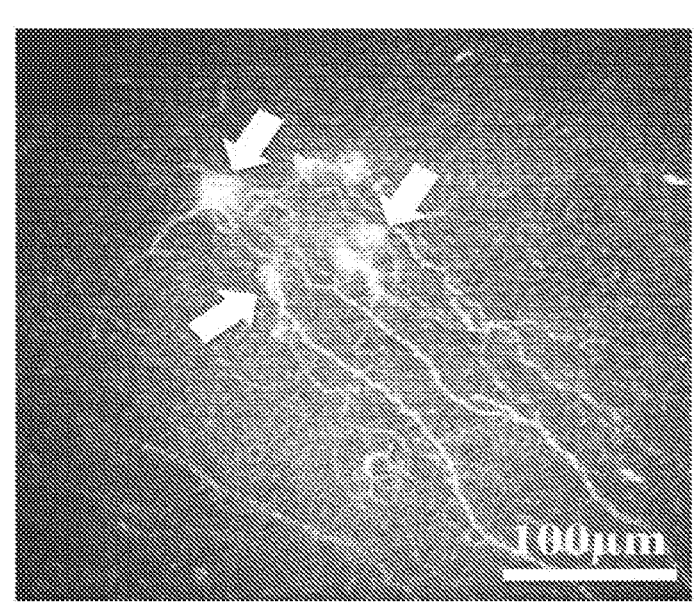

IVCM analysis of nerve density, length of the nerve fibers including main nerve trunks and branches ($mm/mm^2$), was performed using the semi-automated tracing plugin NeuronJ (Image J) in a masked fashion by two observers. Microneuromas were defined as hyper-reflective swellings of injured nerve endings and neurite sprouting, not noted in normal IVCM images of the subbasal plexus, as shown in FIGS. 6A-6B.

Results

The demographics of the 99-member subject pool are provided in Table 2.

TABLE 2

Demographics of the 99-Member Subject Pool Used in This Study

| | Normal (n = 26) | CLW: Asymptomatic (n = 18) | CLW: Symptomatic (n = 19) | CLW: Intolerant (n = 18) | Neuropathic Corneal Pain (n = 18) | P |
|---|---|---|---|---|---|---|
| Age (Mean ± SD) | 38.9 ± 14.0 | 37.3 ± 10.7 | 36.2 ± 13.5 | 35.1 ± 11.0 | 44.7 ± 13.3 | 0.19 |
| Gender (% Female) | 53.8 | 61.1 | 57.9 | 72.2 | 83.3 | 0.29 |

The results of the various questionnaires administered to the 99-member subject pool are provided in Table 3. The results from Table 3 indicate a significant incremental increase in OSDI along the study groups.

TABLE 3

Results of the VAS, CLDEQ-8, and ODSI Questionnaires Provided to the 99-Member Subject Pool

| | Normal (n = 26) | CLW: Asymptomatic (n = 18) | CLW: Symptomatic (n = 19) | CLW: Intolerant (n = 18) | Neuropathic Corneal Pain (n = 18) | P |
|---|---|---|---|---|---|---|
| VAS | 0.0 ± 0.0 | 0.0 ± 0.0 | 2.6 ± 3.2*† | 2.7 ± 2.2*† | 5.4 ± 2.7*†‡# | <0.001 |
| CLDEQ-8 | 0.0 ± 0.0 | 6.3 ± 4.5* | 21.9 ± 7.8*† | 19.4 ± 7.0*† | 5.5 ± 7.9*†# | <0.001 |
| OSDI | 1.7 ± 3.3 | 5.6 ± 7.6 | 29.7 ± 21.6*† | 25.3 ± 17.7*† | 63.9 ± 26.0*†‡# | <0.001 |

*$p < 0.05$ compared to Normal,
†$p < 0.05$ compared to CLW: Asymptomatic,
‡$p < 0.05$ compared to CLW: Symptomatic;
$p < 0.05$ compared to CLW: Intolerant;
Mean ± SD, multiple comparisons, LSD post-hoc Table 4 present the results of a cold response nociceptive functional test administered to the 99-member subject pool. The data from Table 5 indicates no significance in cold response was noted in subjects having had corneal nociceptive functional testing performed.

TABLE 4

Results of the Cold Response Nociceptive Functional Test Administered to the 99-Member Subject Pool

| | Normal (n = 18) | CLW: Asymptomatic (n = 18) | CLW: Symptomatic (n = 19) | CLW: Intolerant (n = 16) | Neuropathic Corneal Pain (n = 12) | P |
|---|---|---|---|---|---|---|
| Cold Response (change in VAS) | 0.0 ± 0.0 | −0.1 ± 0.5 | −0.4 ± 1.1 | −0.1 ± 0.7 | −0.3 ± 1.4 | NS |

Figure 7:
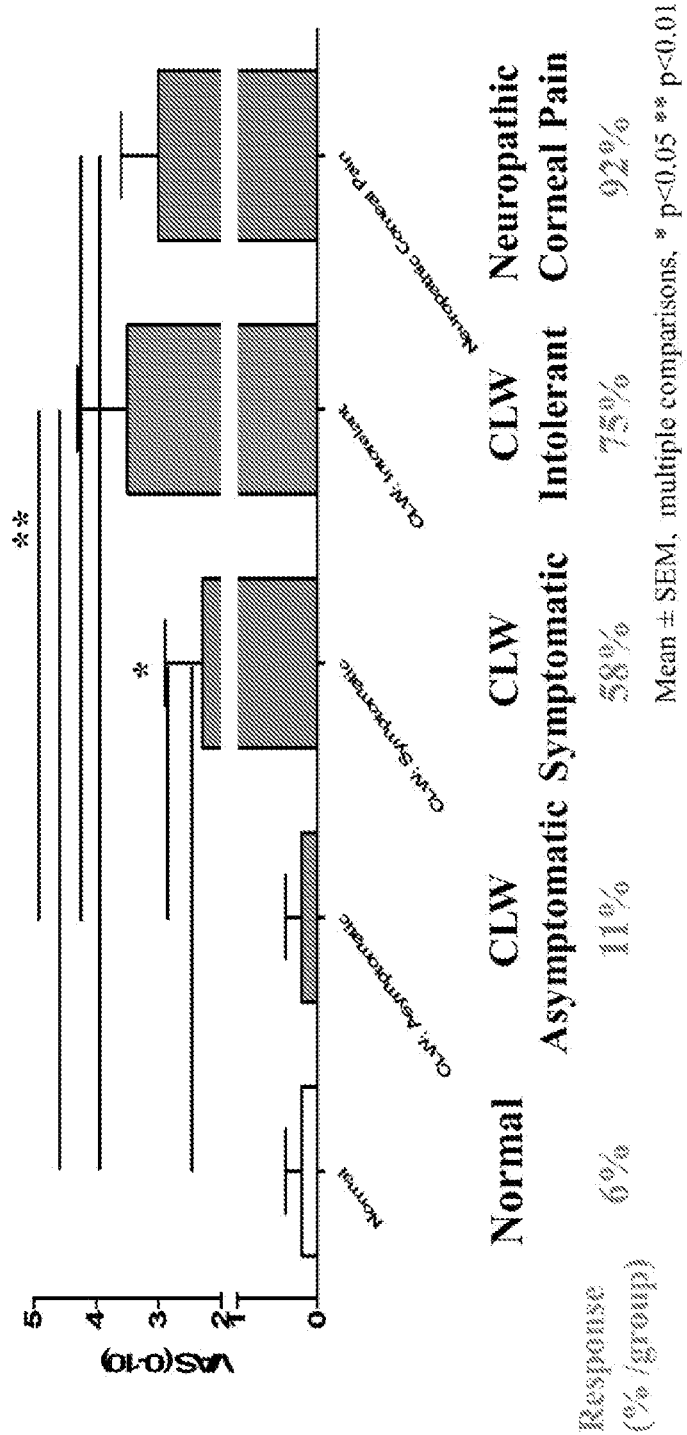
FIG. 7: A graph showing VAS(0-10) of normal, CLW asymptomatic, CLW symptomatic, CLW intolerant, and NCP subjects.
Figure 8:
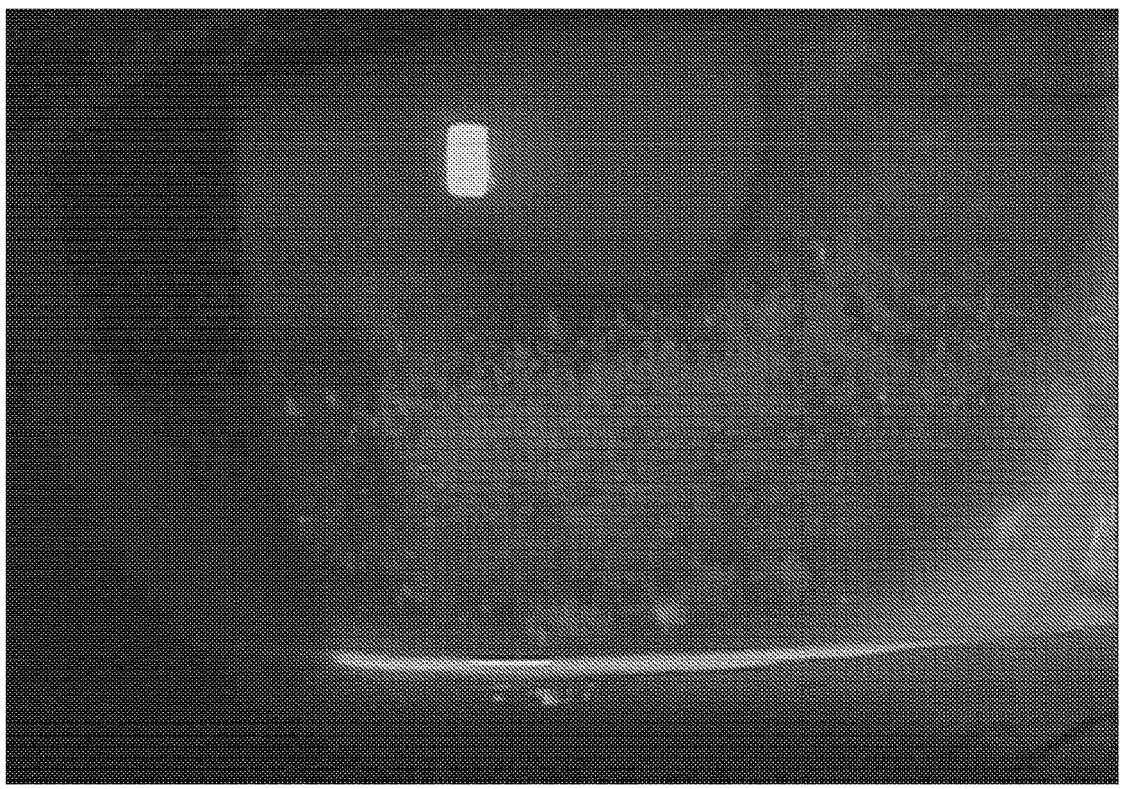
FIG. 8: Representative image of a corneal fluorescent stain.
Figure 9:
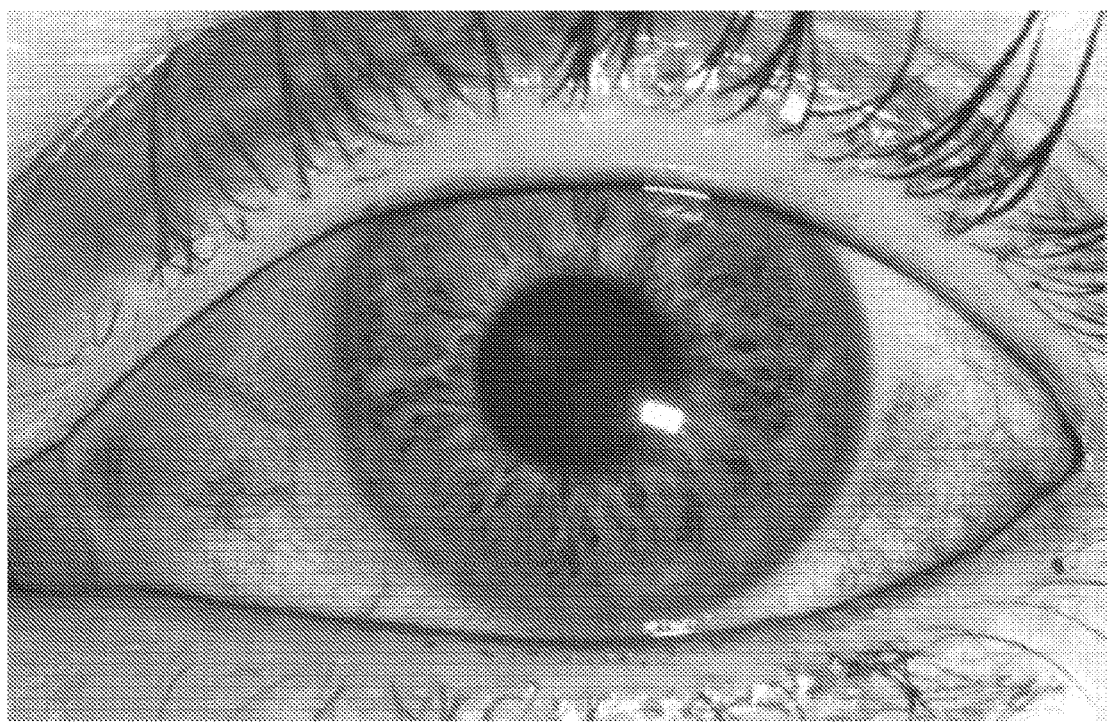
FIG. 9: Representative image of a conjunctival lissamine green stain.
Figure 10:
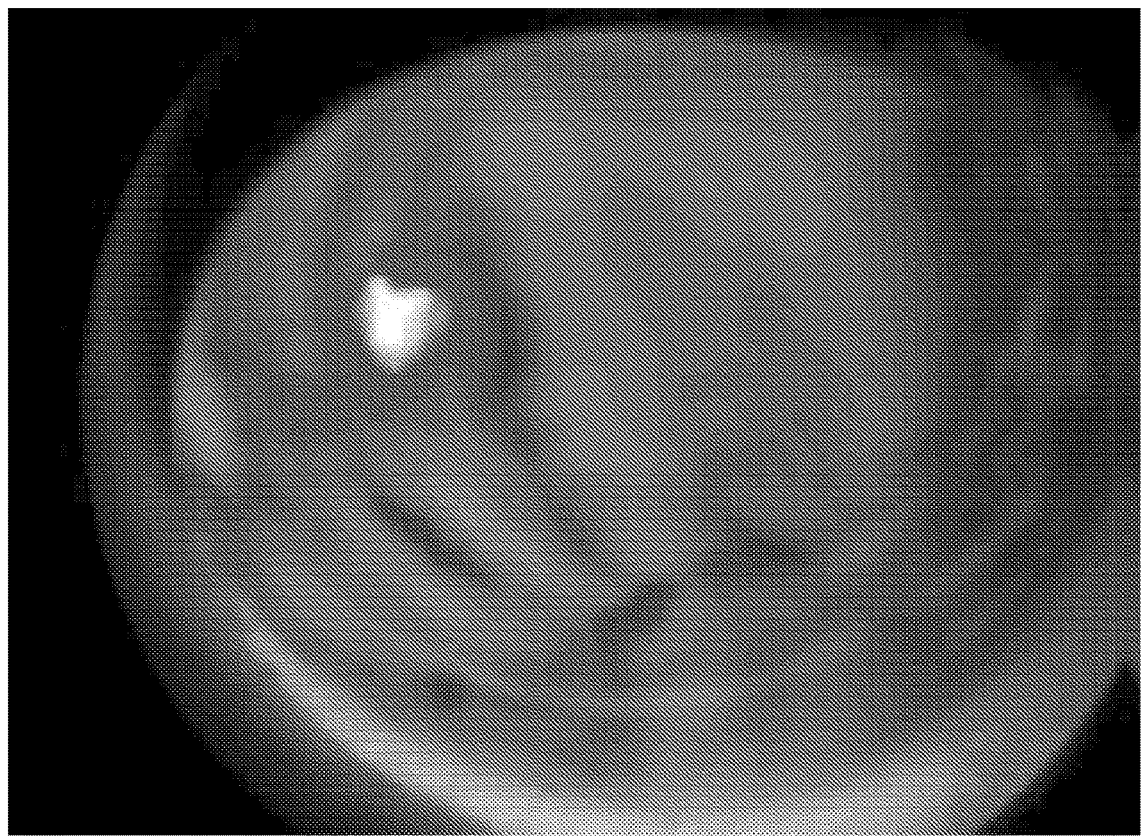
FIG. 10: Representative image of a tear break up test.
Figure 11:
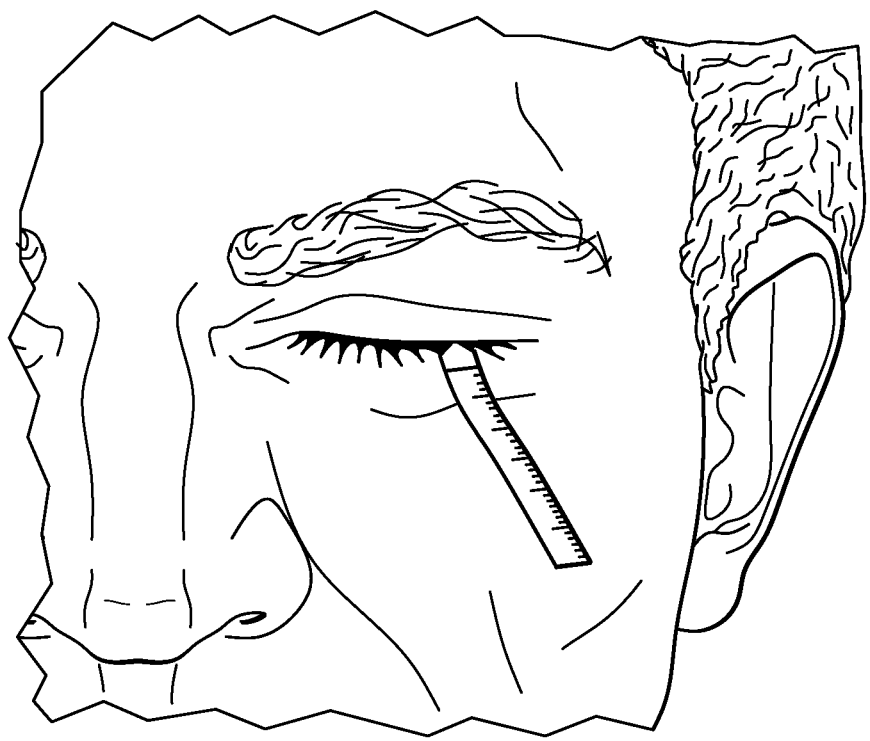
FIG. 11: Representative image of a Schirmer's test.

FIG. 7 shows the results of the HS Response nociceptive functional test administered to the 99-member subject pool.

As is seen in FIG. 7, significant response to HS was noted in symptomatic subjects having had corneal nociceptive functional testing performed, with response frequency incrementally increasing across groups.

Table 5 presents the correlations between the results of the OSDI questionnaire and the factors examined, e.g., nerve density, micro-neuromas, HS response, and cold response.

TABLE 5

Correlations Between the Results of the ODSI
Questionnaire and the Factors Examined

|      |                     | Nerve Density | Micro-neuroma | HS response | Cold Response |
|------|---------------------|---------------|---------------|-------------|---------------|
| OSDI | Pearson Correlation | −0.30         | 0.25          | 0.41        | −0.32         |
|      | P (2-tailed)        | 0.01          | 0.006         | 0.0002      | 0.004         |
|      | N                   | 84            | 84            | 79          | 79            |

The results in Table 5 indicate that morphological and functional changes are significantly correlated with worsening of OSDI scores across groups; the most significant correlation being with HS response. Further, the results in table 5 indicate that the frequency of micro-neuroma and HS responses were similar among symptomatic subjects (81.0% and 72.0%, respectively).

Conclusion

The data presented in this Example highlights the presence of morphological and functional alterations even in the CLW: Asymptomatic group (i.e., the presence of micro-neuromas indicates functional nerve alterations precede ocular symptoms), although a larger number of subjects demonstrated presence of micro-neuromas. The response to hyperosmolar saline (HS) appears to be a better indicator of abnormal neuronal function compared to cold saline. Functional testing combined with morphological alterations of corneal nerves may allow for identification of patients with neurosensory abnormalities and at risk for development of symptoms of discomfort and pain.

Example 3—Patients with Clinical Signs of Dry Eye Disease Demonstrate Presence of Signs of Neuropathic Corneal Pain In the experiments described in this Example, we investigated how or if clinical signs of dry eye disease (DED) can coexist with micro-neuromas, as seen by IVCM in patients with neuropathic corneal pain (NCP). DED was recently re-defined by the Dry Eye Workshop (DEWS) II report as 'a multifactorial disease of the ocular surface characterized by a loss of homeostasis of the tear film, and accompanied by ocular symptoms, in which tear film instability and hyperosmolarity, ocular surface inflammation and damage, and neurosensory abnormalities play etiological roles'.

According to DEWS II, clinical signs related to DED may also occur with various other ocular surface diseases. Therefore, DED is usually treated as a diagnosis of exclusion in patients with clinical signs in concordance with or without presence of symptoms. On the other hand, patients with symptoms without demonstrable ocular signs are not categorized in the DED group, but are differentiated into pre-clinical ocular surface disease or neuropathic pain, also referred as non-ocular surface disease.

The International Association for the Study of Pain (IASP) defines neuropathic pain as "pain initiated or caused by a primary lesion or dysfunction of the nervous system." The diagnosis of neuropathic pain requires confirmation of injury or disease affecting somatosensory pathways of peripheral and/or central nervous systems.

NCP is a recently acknowledged ocular condition that can be defined as symptoms perceived such as pain, discomfort, burning, allodynia, or photophobia caused by dysfunctional nerves following damage to the trigeminal nerve endings in the cornea. The diagnosis of NCP currently requires the combination of ocular history, symptoms, lack of significant clinical signs, and objective confirmation of nerve injury. However, discordance between symptoms and signs has also been suggested as a possible indicator.

The evidence of corneal nerve alterations obtained via IVCM imaging can provide valuable information as supporting data for the diagnosis of NCP. Various studies have looked at the correlations between subbasal nerve alterations, such as reduced density and increased tortuosity and beading, and clinical signs and symptoms of DED. Similar to patients with DED, NCP patients also demonstrate corneal nerve alterations, including increased beading and reflectivity and a more profound loss of subbasal nerves. The data shows that NCP patients present with micro-neuromas, swelling of nerve terminals, as seen by IVCM, suggesting they can be indicative of specific nerve alterations and potential optical biomarkers seen in these patients.

Methods

For the assessment of whether the clinical signs of dry eye disease (DED) can coexist with micro-neuromas, as seen by IVCM in patients with neuropathic corneal pain (NCP), we performed a cross-sectional, controlled, single center study of 91 subjects. The study assessed the following clinical signs for DED (see FIGS. 8-11):

Corneal fluorescein staining (CFS)≥1 (NEI scale)
Conjunctival lissamine green staining (LGS)≥1 (NEI scale)
Fluorescein tear break-up time (TBUT)<10 seconds
Schirmer's test≤10 mm
Presence of micro-neuromas as imaged by IVCM.

Ocular discomfort levels were also assessed by visual analogue scale (VAS, range 0-10) for each subject in writing. Eighty-four subjects that had at least one clinical sign and/or micro-neuromas were included in the analyses.

Results

Table 6 shows the demographics of the 91-member subject pool used in this study.

TABLE 6

Demographics of the 91-Member Subject Pool Used in This Study

|        | Number of Subjects | Mean age (years) | Standard Deviation |
|--------|--------------------|------------------|--------------------|
| Male   | 57                 | 40.01            | 13.39              |
| Female | 27                 | 37.77            | 11.48              |
| Total  | 84                 | 39.29            | 12.78              |

Table 7 presents the results of the DED clinical evaluations as described herein for the 91-member subject pool used in this study.

TABLE 7

Frequency of Concomitant Presence of Micro-Neuromas in Subjects with Clinical Signs of DED

|                          | CFS ≥1 (n = 35) | LGS ≥1 (n = 51) | TBUT <10 seconds (n = 46) | Schrimer's Test ≤10 mm (n = 32) |
|--------------------------|-----------------|-----------------|---------------------------|----------------------------------|
| Micro-neuroma present    | 24 (68.6%)      | 30 (58.8%)      | 31 (67.4%)                | 18 (56.3%)                       |
| Micro-neuroma absent     | 11 (31.4%)      | 21 (41.2%)      | 15 (32.2%)                | 14 (43.8%)                       |

Seventy six subjects out of the 84 that were eligible for analyses, had one or more co-existing clinical signs of DED

[35 (41.7%) had CFS 1/15, 51 (60.7%) had LGS 1/18, 46 (54.8%) had TBUT <10 seconds and 32 (38.1%) Schirmer's test ≤10 mm]. The frequencies of concomitant presence of micro-neuromas with clinical signs of DED were 24 (68.6%) for CFS, 30 (58.8%) for LGS, 31 (67.4%) for TBUT and 18 (56.3%) for Schirmer's test respectively. Of 54 (64.3%) subjects presenting with micro-neuromas, 46 (85.2%) had one or more concomitant clinical signs of DED. Twenty four (44.4%) subjects had CFS ≥1/15, 30 (55.6%) had LGS ≥1/18, 31 (57.4%) had TBUT <10 seconds and 18 (33.3%) had Schirmer's test s 10 mm.

Figure 12:
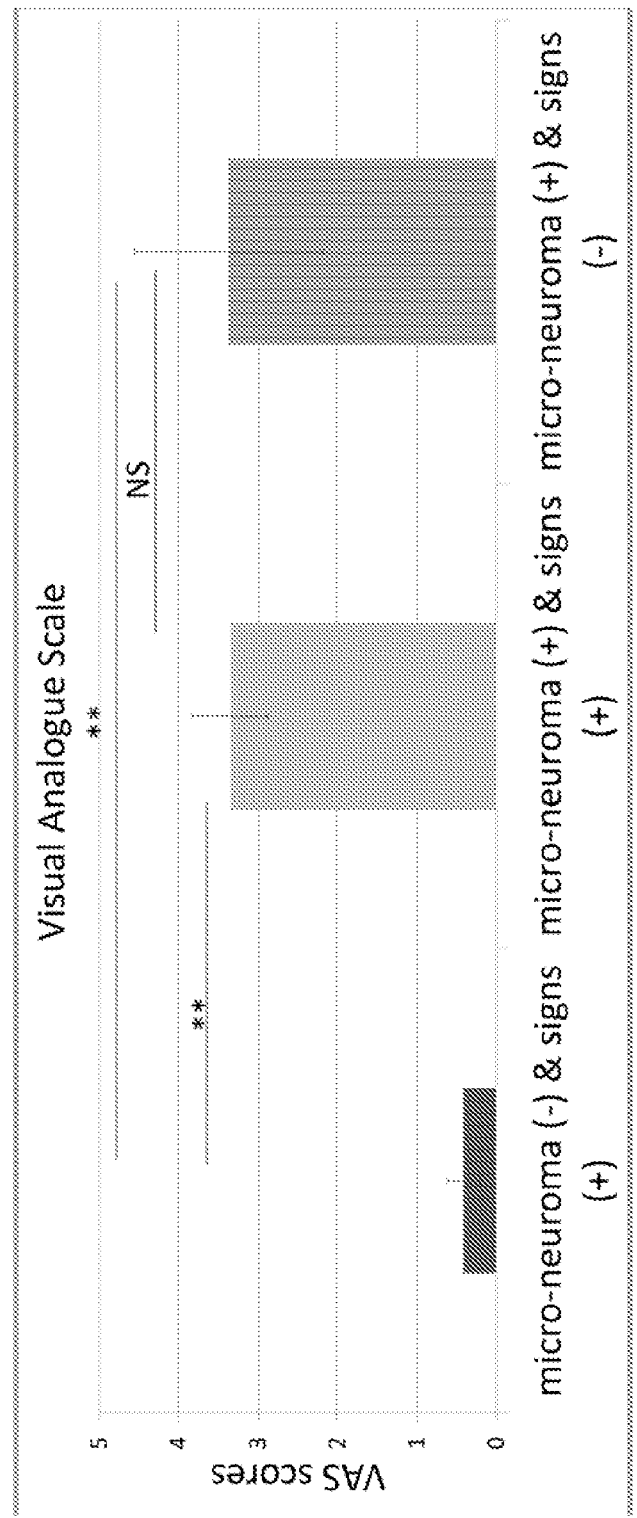
FIG. 12: Mean VAS scores in relation to the concomitant presence of micro-neuromas and clinical signs of DED.

Additionally, the level of pain/discomfort in these subjects were evaluated, by assessing the mean VAS scores, as shown in FIG. 12. For subjects without micro-neuromas presenting with one or more clinical DED signs (n=29) the VAS was 0.41±0.20, and for the subjects presenting with micro-neuromas it was significantly higher [3.35±3.12 ($p<0.001$) and 3.37±1.19 ($p=0.015$) with (n=42) and without (n=8) concomitant clinical DED signs, respectively].

Conclusion

IVCM has been shown to be a beneficial tool for imaging the corneal sub-basal nerve layer comparable to ex-vivo histochemical techniques. It also has the potential to be used as a supporting diagnostic tool, as it allows the visualization of nerve alterations, particularly presence micro-neuromas. This study demonstrates that signs of DED can coexist with micro-neuromas that were previously seen in NCP patients and not in conventional DED patients. Morphological corneal nerve abnormalities, as confirmed on IVCM, may mediate the symptoms of discomfort in patients with clinical signs of DED.

List of Certain Embodiments

Certain embodiments of the invention are within the scope of the following numbered paragraphs.

1. A system for determining of the presence of at least one neuroma on an ocular surface of a subject, the system comprising:
  a) an in vivo confocal microscope configured to produce an image of at least a portion of the ocular surface; and
  b) a computer programmed to determine the presence of at least one neuroma on the ocular surface from input data corresponding to the image produced by the in vivo confocal microscope.

2. The system of paragraph 1, wherein the neuroma is a micro-neuroma.

3. The system of paragraph 1, wherein the ocular surface is the corneal surface.

4. The system of paragraph 1, wherein the computer is programmed with a neural network.

5. The system of paragraph 4, wherein the neural network is a multilayer perceptron.

6. The system of paragraph 5, wherein the multilayer perceptron comprises:
  a) a plurality of input nodes, wherein each input node is configured to contain at least one data point;
  b) a plurality of hidden nodes grouped in at least one layer, wherein each of the plurality of hidden nodes receives as input all of the at least one data points from the plurality of input nodes; and
  c) a plurality of output nodes, wherein the plurality of hidden nodes and plurality of output nodes are trained with a plurality of images of an ocular surface.

7. The system of paragraph 6, wherein the plurality of hidden nodes further comprises a transfer function to determine the presence of at least one micro-neuroma in an eye of a subject.

8. The system of paragraph 7, wherein the derivative of the transfer function is used to update the statistical weights of each of the plurality of hidden nodes.

9. The system of paragraph 7 or 8, wherein the transfer function is a sigmoid function.

10. The system of paragraph 6, wherein the plurality of output nodes further comprises a sigmoid transfer function.

11. The system of any one of paragraphs 4-10, wherein the neural network is trained using a plurality of images of an ocular surface from a population of subjects.

12. The system of paragraph 11, wherein the number of images of the ocular surface used to train the neural network is at least 1,000.

13. The system of paragraph 11, wherein the number of images of the ocular surface used to train the neural network is at least 10,000.

14. The system of any one of paragraphs 11-13, wherein a portion of the plurality of images of the ocular surface comprises images of micro-neuromas.

15. The system of any one of paragraphs 4-14, wherein the input data for the neural network is a function of the response of the in vivo confocal microscope.

16. The system of paragraph 15, wherein the input data for the neural network is normalized to values between 0-1.

17. The system of any one of paragraphs 6-16, wherein the plurality of output nodes return a value representative of the presence of a micro-neuroma on an ocular surface of a subject.

18. The system of any one of paragraphs 1-17, wherein the computer communicates wirelessly with the in vivo confocal microscope.

19. The system of any one of paragraphs 1-17, wherein the computer is directly connected to the in vivo confocal microscope.

20. The system of any one of paragraphs 1-17, wherein the computer is part of the in vivo confocal microscope.

21. The system of any one of paragraphs 1-17, wherein the computer communicates remotely with the in vivo confocal microscope.

22. A method of identifying the presence of a neuroma on an ocular surface of a subject, comprising:
  a) directing light from an in vivo confocal microscope onto the ocular surface of the subject to produce an image of at least a portion of the ocular surface;
  b) sending the image to a computer programmed with a neural network to determine the presence of a neuroma; and
  c) storing or providing the result of part b) to a user.

23. The method of paragraph 22, wherein the neuroma is a micro-neuroma.

24. The method of paragraph 22 or 23, wherein the ocular surface is the corneal surface.

25. The method of any one of paragraphs 22-24, wherein the neural network is trained using a plurality of images of an ocular surface from a population of subjects.

26. The method of paragraph 25, wherein the number of images of the ocular surface from the population of subjects used to train the neural network is at least 1,000.

27. The method of paragraph 25, wherein the number of images of the ocular surface from the population of subjects used to train the neural network is at least 10,000.

28. The method of any one of paragraphs 25-28, wherein a portion of the plurality of images of ocular surface from the population of subjects comprises images of micro-neuromas.

29. A method of differentially diagnosing neuropathic corneal pain from another ocular indication in a subject, comprising:
   a) acquiring an image of at least a portion of an ocular surface of the subject;
   b) sending the image to a computer programmed to provide an analysis of the ocular surface; and
   c) storing or displaying the image and/or analysis of the ocular surface to a user,
wherein the resulting image and/or analysis of the ocular surface indicates the presence or absence of at least one parameter associated with neuropathic corneal pain.

30. The method of paragraph 29, wherein the other ocular indication is selected from dry eye disease, complications from refractive surgery, ocular effects of Sjögren's Syndrome, neuralgia associated with herpes viruses, chemical irritations, side effects of pharmaceuticals, chemotherapy, and radiation therapy.

31. The method of paragraph 29 or 30, wherein the ocular surface is the corneal surface.

32. The method of any one of paragraphs 29-31, further comprising administration of a therapeutic agent suitable for treating neuropathic corneal pain.

33. The method of paragraph 32, wherein the therapeutic agent is administered ocularly, parenterally, or orally.

34. The method of paragraph 33, wherein the therapeutic agent for ocular or parenteral administration is selected from the group consisting of autologous serum tears, corticosteroids, cryopreserved amniotic membrane, protective contact lenses, scleral lenses, and artificial tears.

35. The method of paragraph 33, wherein the therapeutic agent for oral administration is selected from the group consisting of tricyclic antidepressants, anticonvulsants, opioid antagonists, opioid agonists, GABA inhibitors, serotonin-norepinephrine reuptake inhibitor, transient receptor potential vanilloid (TRPV) receptor antagonists, transient receptor potential melastatin (TRPM) receptor antagonists, and sodium channel blockers.

36. The method of any one of paragraphs 29-35, further comprising at least one parallel diagnosis test.

37. The method of paragraph 36, wherein the at least one parallel diagnosis test is selected from the group consisting of an ocular pain questionnaire, functional somatosensory testing, and a physical eye examination.

38. The method of any one of paragraphs 29-37, wherein the image is acquired using in vivo confocal microscopy.

39. The method of any one of paragraphs 29-38, wherein the computer is programmed with a neural network.

40. The method of any one of paragraphs 29-39, wherein the at least one parameter associated with neuropathic corneal pain is an anatomical structure.

41. The method of paragraph 40, wherein the anatomical structure is a neuroma.

42. The method of paragraph 41, wherein the neuroma is a micro-neuroma.

43. The method of any one of paragraphs 39 to 42, wherein the neural network is trained using a plurality of images of an ocular surface from a population of subjects.

44. The method of paragraph 43, wherein the number of images of the ocular surface from the population of subjects used to train the neural network is at least 1,000.

45. The method of paragraph 43, wherein the number of images of the ocular surface from the population of subjects used to train the neural network is at least 10,000.

46. The method of any one of paragraphs 43-45, wherein a portion of the plurality of images of the ocular surface from the population of subjects comprises images of micro-neuromas.

47. A method of assessing a treatment regimen for neuropathic corneal pain, comprising:
   a) acquiring a first set of in vivo confocal microscopy images of an ocular surface of a subject experiencing neuropathic corneal pain;
   b) analyzing the first set of in vivo confocal microscopy images using a computer programmed with a neural network to identify an anatomical structure associated with neuropathic corneal pain;
   c) administering a therapeutic agent suitable for treating neuropathic corneal pain to the subject for a therapeutically sufficient duration;
   d) acquiring a second set of in vivo confocal microscopy images of the ocular surface of the subject;
   e) analyzing the second set of in vivo confocal microscopy images using a computer programmed with a neural network to determine structural changes in the anatomical structure associated with neuropathic corneal pain; and
   f) repeating steps a-e until the subject experiences a reduction in neuropathic corneal pain, wherein the reduction of neuropathic pain is caused by a reduction in at least one dimension of the anatomical structure identified by the in vivo confocal microscopy imaging.

48. The method of paragraph 47, wherein the ocular surface is the corneal surface.

49. The method of paragraph 47 or 48, wherein the anatomical structure is a neuroma.

50. The method of paragraph 49, wherein the neuroma is a micro-neuroma.

51. The method of any one of paragraphs 47-50, wherein the neural network is trained using a plurality of images of an ocular surface from a population of subjects.

52. The method of paragraph 51, wherein the number of images of the ocular surface from the population of subjects used to train the neural network is at least 1,000.

53. The method of paragraph 51, wherein the number of images of the ocular surface from the population of subjects used to train the neural network is at least 10,000.

54. The method of any one of paragraphs 51-53, wherein a portion of the plurality of images of the ocular surface from the population of subjects comprises images of micro-neuromas.

55. The method of any one of paragraphs 47-54, wherein the therapeutic agent is administered ocularly, parenterally, or orally.

56. The method of paragraph 55, wherein the therapeutic agent for ocular or parenteral administration is selected from the group consisting of tricyclic antidepressants, anticonvulsants, autologous serum tears, corticosteroids, cryopreserved amniotic membrane, amniotic fluid, protective contact lenses, scleral lenses, and artificial tears.

57. The method of paragraph 55, wherein the therapeutic agent for oral administration is selected from the group consisting of tricyclic antidepressants, anticonvulsants, opioid antagonists, opioid agonists, GABA inhibitors, serotonin-norepinephrine reuptake inhibitor, transient receptor potential vanilloid (TRPV) receptor antagonists, transient receptor potential melastatin (TRPM) receptor antagonists, and sodium channel blockers.

58. The method of any one of paragraphs 47-57, wherein the therapeutically sufficient duration is at least 2 weeks.

59. A method of determining the efficacy of a treatment for neuropathic corneal pain, comprising:
  a) diagnosing a subject as having or potentially having neuropathic corneal pain;
  b) acquiring a first set of in vivo confocal microscopy images of an ocular surface of the subject;
  c) analyzing the first set of in vivo confocal microscopy images using a computer programmed with a neural network to identify at least one parameter associated with neuropathic corneal pain;
  d) administering a therapeutic agent to the subject;
  e) acquiring a second set of in vivo confocal microscopy images of the ocular surface of the subject;
  f) analyzing the second set of in vivo confocal microscopy images using a computer programmed with a neural network to determine a change in the at least one parameter associated with neuropathic corneal pain; and
  g) storing or providing an output indicative of the efficacy of the treatment for neuropathic corneal pain.

60. The method of paragraph 59, wherein the ocular surface is the corneal surface.

61. The method of paragraph 59 or 60, wherein the at least one parameter associated with neuropathic corneal pain is an anatomical structure.

62. The method of paragraph 61, wherein the anatomical structure is a neuroma.

63. The method of paragraph 62, wherein the neuroma is a micro-neuroma.

64. The method of any one of paragraphs 59-63, wherein the neural is trained using a plurality of images of an ocular surface from a population of subjects.

65. The method of paragraph 64, wherein the number of images of the ocular surface from the population of subjects used to train the neural network is at least 1,000.

66. The method of paragraph 64, wherein the number of images of the ocular surface from the population of subjects used to train the neural network is at least 10,000.

67. The method of any one of paragraphs 64-66, wherein a portion of the plurality of images of the ocular surface from the population of subjects comprises images of micro-neuromas.

68. The method of any one of paragraphs 59-67, wherein the therapeutic agent for neuropathic corneal pain is selected from tricyclic antidepressants, anticonvulsants, nerve growth factors, naltrexone, amniotic membrane gel, cryopreserved amniotic membranes, amniotic fluid, dual enkephalinase inhibitors, Tivanisiran (Syl1001), anti-inflammatories, immunosuppressives, lifitegrast, transient receptor potential vanilloid (TRPV) receptor antagonists, transient receptor potential melastatin (TRPM) receptor antagonists, or neuroregeneratives.

69. The method of any one of paragraphs 59-68, wherein the change in the at least one parameter associated with neuropathic corneal pain comprises a reduction in at least one dimension of the anatomical structure.

70. The method of any one of paragraphs 59-69, wherein providing the output comprises displaying a representation of the data from the neural network to a user on a display device.

71. A non-transitory computer readable medium having instructions stored thereon, wherein the instructions, when executed by a processor, perform a method for automatically determining the presence of at least one neuroma on at least one image of an ocular surface of a subject, the method comprising:
  a) acquiring at least one image of an ocular surface of a subject; and
  b) determining the presence of a neuroma on the at least one image of an ocular surface of a subject by analyzing the at least one image of an ocular surface of a subject using a trained neural network, wherein the trained neural network comprises:
    i) a residual learning architecture; and
    ii) a backpropagation algorithm comprising a gradient descent optimizer, wherein the neural network is trained using a plurality of images of an ocular surface from a population of subjects, wherein the plurality of images of an ocular surface from a population of subjects are augmented using data blending augmentation such as mix-up or data interpolating augmentation prior to training the neural network.

72. The non-transitory computer readable medium of paragraph 71, wherein the at least one image of an ocular surface of a subject are acquired using an in vivo confocal microscope.

73. The non-transitory computer readable medium of paragraph 71 or 72, wherein the plurality of images of an ocular surface from a population of subjects used to train the neural network are pre-processed by normalizing each image against parameters from an image database.

74. The non-transitory computer readable medium of any one of paragraphs 71-73, wherein the plurality of images of an ocular surface from a population of subjects used to train the neural network are pre-processed by conversion of a grayscale single channel pixel intensity to a three channel RGB color pixel intensity.

75. The non-transitory computer readable medium of any one of paragraphs 71-74, wherein the plurality of images of an ocular surface from a population of subjects used to train the neural network are further augmented prior to training the neural network by random image flipping, random image rotation, random image crops, or a combination thereof.

76. The non-transitory computer readable medium of any one of paragraphs 71-75, wherein the neural network further comprises batch normalization.

77. The non-transitory computer readable medium of any one of paragraphs 71-76, wherein the neural network further comprises Dropout regularization.

78. The non-transitory computer readable medium of any one of paragraphs 71-77, wherein the residual learning architecture comprises an input layer, an output layer, and from 2 to 100 hidden layers.

79. The non-transitory computer readable medium of paragraph 78, wherein the total number of layers of the residual learning architecture is between 40 to 60.

80. The non-transitory computer readable medium of any one of paragraphs 71-79, wherein the gradient descent optimizer comprises stochastic gradient descent.

81. The non-transitory computer readable medium of any one of paragraphs 71-80, wherein gradient descent optimizer comprises a learning rate from about 0.000001 to about 0.1.

82. The non-transitory computer readable medium of paragraph 81, wherein the learning rate is 0.00001.

83. The non-transitory computer readable medium of any one of paragraphs 71-82, wherein gradient descent optimizer further comprises momentum gradient acceleration.

84. The non-transitory computer readable medium of paragraph 83, wherein the momentum gradient acceleration has a value from 0 to about 1.

85. The non-transitory computer readable medium of paragraph 83 or 84, wherein the momentum gradient acceleration has a value of 0.9.

86. The non-transitory computer readable medium of any one of paragraphs 71-85, wherein the neuroma is a micro-neuroma.

87. The non-transitory computer readable medium of any one of paragraphs 71-86, wherein the number of images of the ocular surface from the population of subjects used to train the neural network is at least 1,000.

88. The non-transitory computer readable medium of any one of paragraphs 71-86, wherein the number of images of the ocular surface from the population of subjects used to train the neural network is at least 10,000.

89. The non-transitory computer readable medium of any one of paragraphs 71-88, wherein a portion of the plurality of images of the ocular surface from the population of subjects used to train the neural network comprises images of micro-neuromas.

90. A non-transitory computer readable medium having instructions for analyzing an image of an ocular surface stored thereon, comprising:
   a) a neural network comprising:
      i) a pre-trained residual learning architecture comprising about 50 layers, wherein the residual learning architecture was pre-trained with at least one of images from an image database or a plurality of images of an ocular surface from a population of subjects;
      ii) batch normalization;
      iii) Dropout regularization; and
      iv) data augmentation prior to analysis by the residual learning architecture, wherein the data augmentation comprises data blending augmentation or data interpolating augmentation, which optionally is selected from at least one of mixup, random image flipping, random image rotation, or random image crops; and
   b) a backpropagation algorithm comprising:
      i) stochastic gradient descent, wherein the stochastic gradient descent further comprises momentum gradient acceleration with a value of 0.9; and
      ii) a learning rate of 0.00001.

91. A method of identifying a micro-neuroma in an image of an ocular surface of a subject, comprising analyzing the image of the ocular surface of the subject using a non-transitory computer readable medium having instructions stored thereon of any one of paragraphs 71-90.

92. The method or system of any one of paragraphs 1 to 70, which utilizes a non-transitory computer readable medium selected from those of any one of paragraphs 71 to 91.

93. A method of diagnosing NCP, the method comprising detection of micro-neuromas on the ocular surface of the eye of a patient, e.g., as described herein, optionally in combination with one or more additional steps of clinical assessment.

94. The method of paragraph 93, further comprising the use of one or more of (i) symptom questionnaire(s), (ii) functional somatosensory testing (e.g., proparacaine challenge test, corneal esthesiometry, or other nerve function tests), (iii) clinical examination (e.g., assessment of signs of ocular surface disease), (iv) assessment of ocular co-morbidities (e.g., Meibomian gland dysfunction, ocular allergy, conjuctivochalasis, and/or recurrent erosion syndrome), and (v) assessment of nerve density and morphology (e.g., detection of neuromas, such as micro-neuromas).

95. The method of paragraph 94, wherein assessment of nerve morphology comprises the detection of micro-neuromas, optionally using a system as described herein.

96. A method of determining the cause of contact lens discomfort in a subject, the method comprising determining whether the cornea of the subject comprises one or more micro-neuromas.

97. A method for determining whether a subject may be at risk of developing contact lens discomfort, the method comprising determining whether the cornea of the subject comprises one or more micro-neuromas.

98. The method of paragraph 96, wherein the method comprises the use of a system of any one of paragraphs 1 to 70, or a non-transitory computer readable medium selected from those of any one of paragraphs 71 to 91.

99. The method of paragraph 97, wherein the method comprises the use of a system of any one of paragraphs 1 to 70, or a non-transitory computer readable medium selected from those of any one of paragraphs 71 to 91.

Other embodiments are within the scope of the claims.

What is claimed is:

1. A method of (i) identifying the presence of a neuroma on an ocular surface of a subject, or (ii) differentially diagnosing neuropathic corneal pain from another ocular indication in a subject, wherein the method of part (i) comprises:
   a) directing light from an in vivo confocal microscope onto the ocular surface of the subject to produce an image of at least a portion of the ocular surface;
   b) sending the image to a computer programmed with a neural network to determine the presence of a neuroma; and
   c) storing or providing the result of part b) to a user, and the method of part (ii) comprises:
   a) acquiring an image of at least a portion of an ocular surface of the subject;
   b) sending the image to a computer programmed to provide an analysis of the ocular surface; and
   c) storing or displaying the image and/or analysis of the ocular surface to a user,
   wherein the resulting image and/or analysis of the ocular surface indicates the presence or absence of at least one parameter associated with neuropathic corneal pain.

2. The method of claim 1, wherein the neuroma is a micro-neuroma.

3. The method of claim 1, wherein the ocular surface is the corneal surface.

4. The method of claim 1, wherein the neural network is trained using a plurality of images of an ocular surface from a population of subjects.

5. A method of (i) assessing a treatment regimen for neuropathic corneal pain, or (ii) for determining the efficacy of a treatment for neuropathic corneal pain, wherein the method of part (i) comprises:
   a) acquiring a first set of in vivo confocal microscopy images of an ocular surface of a subject experiencing neuropathic corneal pain;
   b) analyzing the first set of in vivo confocal microscopy images using a computer programmed with a neural network to identify an anatomical structure associated with neuropathic corneal pain;
   c) administering a therapeutic agent suitable for treating neuropathic corneal pain to the subject for a therapeutically sufficient duration;
   d) acquiring a second set of in vivo confocal microscopy images of the ocular surface of the subject;

e) analyzing the second set of in vivo confocal microscopy images using a computer programmed with a neural network to determine structural changes in the anatomical structure associated with neuropathic corneal pain; and f) repeating steps a-e until the subject experiences a reduction in neuropathic corneal pain, wherein the reduction of neuropathic pain is caused by a reduction in at least one dimension of the anatomical structure identified by the in vivo confocal microscopy imaging, and the method of part (ii) comprises:

a) diagnosing a subject as having or potentially having neuropathic corneal pain;

b) acquiring a first set of in vivo confocal microscopy images of an ocular surface of the subject;

c) analyzing the first set of in vivo confocal microscopy images using a computer programmed with a neural network to identify at least one parameter associated with neuropathic corneal pain;

d) administering a therapeutic agent to the subject;

e) acquiring a second set of in vivo confocal microscopy images of the ocular surface of the subject;

f) analyzing the second set of in vivo confocal microscopy images using a computer programmed with a neural network to determine a change in the at least one parameter associated with neuropathic corneal pain; and g) storing or providing an output indicative of the efficacy of the treatment for neuropathic corneal pain.

6. The method of claim 5, wherein the ocular surface is the corneal surface.

7. The method of claim 5, wherein the anatomical structure is a neuroma.

8. The method of claim 7, wherein the neuroma is a micro-neuroma.

9. The method of claim 5, wherein the neural network is trained using a plurality of images of an ocular surface from a population of subjects.

10. A non-transitory computer readable medium having instructions stored thereon, wherein (I) the instructions, when executed by a processor, perform a method for automatically determining the presence of at least one neuroma on at least one image of an ocular surface of a subject, the method comprising:

a) acquiring at least one image of an ocular surface of a subject; and b) determining the presence of a neuroma on the at least one image of an ocular surface of a subject by analyzing the at least one image of an ocular surface of a subject using a trained neural network, wherein the trained neural network comprises:

i) a residual learning architecture; and ii) a backpropagation algorithm comprising a gradient descent optimizer, wherein the neural network is trained using a plurality of images of an ocular surface from a population of subjects, wherein the plurality of images of an ocular surface from a population of subjects are augmented using data blending augmentation such as mix-up or data interpolating augmentation prior to training the neural network; or (II) the non-transitory computer readable medium comprises:

a) a neural network comprising:

i) a pre-trained residual learning architecture comprising about 50 layers, wherein the residual learning architecture was pre-trained with at least one of images from an image database or a plurality of images of an ocular surface from a population of subjects;

ii) batch normalization;

iii) Dropout regularization; and iv) data augmentation prior to analysis by the residual learning architecture, wherein the data augmentation comprises data blending augmentation or data interpolating augmentation, which optionally is selected from at least one of mixup, random image flipping, random image rotation, or random image crops; and b) a backpropagation algorithm comprising:

i) stochastic gradient descent, wherein the stochastic gradient descent further comprises momentum gradient acceleration with a value of 0.9; and ii) a learning rate of 0.00001.

11. The non-transitory computer readable medium of claim 10, wherein the at least one image of an ocular surface of a subject are acquired using an in vivo confocal microscope.

12. The non-transitory computer readable medium of claim 10, wherein the plurality of images of an ocular surface from a population of subjects used to train the neural network are pre-processed by normalizing each image against parameters from an image database or by conversion of a grayscale single channel pixel intensity to a three channel RGB color pixel intensity.

* * * * *